United States Patent
Clemmer et al.

(10) Patent No.: US 9,683,965 B2
(45) Date of Patent: Jun. 20, 2017

(54) HYBRID ION MOBILITY SPECTROMETER

(71) Applicant: Indiana University Research and Technology Corporation, Indianapolis, IN (US)

(72) Inventors: David E. Clemmer, Bloomington, IN (US); Michael A. Ewing, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 15/023,575

(22) PCT Filed: Sep. 23, 2014

(86) PCT No.: PCT/US2014/056970
§ 371 (c)(1),
(2) Date: Mar. 21, 2016

(87) PCT Pub. No.: WO2015/048014
PCT Pub. Date: Apr. 2, 2015

(65) Prior Publication Data
US 2016/0209363 A1      Jul. 21, 2016

Related U.S. Application Data

(60) Provisional application No. 61/882,891, filed on Sep. 26, 2013.

(51) Int. Cl.
*H01J 49/00* (2006.01)
*G01N 27/62* (2006.01)

(52) U.S. Cl.
CPC ................. *G01N 27/622* (2013.01)

(58) Field of Classification Search
USPC ................ 250/281, 282, 286, 288, 290
See application file for complete search history.

(56) References Cited

U.S. PATENT DOCUMENTS

| | | |
|---|---|---|
| 2007/0278396 A1 | 12/2007 | Wu |
| 2011/0198493 A1 | 8/2011 | Clemmer et al. |
| 2012/0153140 A1 | 6/2012 | Makarov |
| 2012/0273669 A1 | 11/2012 | Ivashin et al. |
| 2013/0161506 A1 | 6/2013 | Ugarov |

OTHER PUBLICATIONS

PCT Search Report and Written Opinion for PCT/U62014/056970, completed Jan. 8, 2015.

*Primary Examiner* — Nicole Ippolito
*Assistant Examiner* — Hanway Chang
(74) *Attorney, Agent, or Firm* — Barnes & Thornburg LLP

(57) ABSTRACT

A hybrid ion mobility spectrometer includes a single-pass drift tube having an ion inlet at one end and an ion outlet at an opposite end, a multiple-pass drift tube having an ion inlet and an ion outlet each coupled to the single pass drift tube between the ion inlet and the ion outlet thereof, and a set of ion gates each controllable between an open position to pass ions therethrough and a closed position to block ions from passing therethrough. The set of ion gates may be controlled to pass at least some ions traveling through the single-pass drift tube into the multiple-pass drift tube via the ion inlet of the multiple-pass drift tube and to pass at least some ions traveling through the multiple-pass drift tube into the single-pass drift tube via the ion outlet of the multiple-pass drift tube.

20 Claims, 7 Drawing Sheets

US 9,683,965 B2

HYBRID ION MOBILITY SPECTROMETER

CROSS-REFERENCE TO RELATED APPLICATION

This patent application is a U. S. national phase of International Application No. PCT/US2014/056970, filed Sep. 23, 2014, which claims the benefit of, and priority to, U.S. patent application Ser. No. 61/882,891, filed Sep. 26, 2013, the disclosures of which are expressly incorporated herein by reference in their entireties.

GOVERNMENT RIGHTS

This invention was made with government support under GM090797 awarded by the National Institutes of Health. The United States Government has certain rights in the invention.

FIELD OF THE INVENTION

This disclosure relates generally to the field of spectrometry, and more specifically to instruments for separating ions in time as a function of ion mobility.

BACKGROUND

Ion mobility spectrometers are analytical instruments used to investigate properties of charged particles by separating the charged particles, i.e., ions, in time as a function of ion mobility. In the typical ion mobility spectrometers, an electric drift field is established in a drift tube filled with a buffer gas, and as the ions move through the drift tube under the influence of the electric drift field the ions collide with the buffer gas and separate as a function their collision cross-sections such that more compact conformers reach the end of the drift tube faster than less compact conformers. Known drift tubes may be so-called single-pass drift tubes, i.e., linear or non-linear drift tubes through which ions traverse only once between ion inlets and outlets thereof, or so-called multiple-pass drift tubes, i.e., linear or closed-path drift tubes through which ions may traverse multiple times before exit.

SUMMARY

The present invention may comprise one or more of the features recited in the attached claims, and/or one or more of the following features and combinations thereof. A hybrid ion mobility spectrometer may comprise a single-pass drift tube having an ion inlet at one end and an ion outlet at an opposite end, a multiple-pass drift tube having an ion inlet and an ion outlet each coupled to the single pass drift tube between the ion inlet of the single-pass drift tube and the ion outlet of the single-pass drift tube, and a set of ion gates each controllable between an open position to pass ions therethrough and a closed position to block ions from passing therethrough. The set of ion gates may be controlled between the open and closed positions to selectively pass at least some of the ions traveling through the single-pass drift tube into the multiple-pass drift tube via the ion inlet of the multiple-pass drift tube and to selectively pass at least some of the ions traveling through the multiple-pass drift tube into the single-pass drift tube via the ion outlet of the multiple-pass drift tube. The single-pass drift tube may be configured to separate in time ions entering the ion inlet thereof and traveling therethrough according to a first function of ion mobility, and the multiple-pass drift tube may be configured to separate in time ions entering the ion inlet thereof and traveling one or more times therethrough according to the first or a second function of ion mobility.

Each of the set of ions gates may be controllable to the open position in response to a different first ion gate control signal and controllable to the closed position in response to a different second ion gate control signal. The hybrid ion mobility spectrometer in this embodiment may further comprise a first plurality of voltage sources to produce the different first and second ion gate control signals. One or more voltage sources within the first plurality of voltage sources may be programmable to control timing of production of at least one of the different first ion gate control signals and at least one of the different second ion gate control signals. The hybrid ion mobility spectrometer may further or alternatively comprise a processor electrically coupled to at least one of the first plurality of voltage sources, and the processor may be configured to control timing of production of at least one of the different first ion gate control signals and at least one of the different second ion gate control signals.

The single-pass drift tube in any of the preceding paragraphs may be responsive to a first set of voltage signals to separate ions in time according to the first function of ion mobility and the multiple-pass drift tube may be responsive to a second set of voltage signals to separate ions in time according to the first or second function of ion mobility, and the hybrid ion mobility spectrometer may further comprise a second plurality of voltage sources to produce the first and second sets of voltage signals. In one embodiment, one or more voltage sources within the second plurality of voltage sources may be programmable to control production of at least one of the first and second sets of voltage signals. Alternatively or additionally, the ion mobility spectrometer may further comprise a processor electrically coupled to at least one of the second plurality of voltage sources, and the processor may be configured to control production of at least one of the first and second sets of voltage signals.

In the hybrid ion mobility spectrometer of any of the preceding paragraphs, each of the set of ion gates may be controllable to at least one intermediate position to pass at least some ions therethrough. One or more of the set of ion gates may be controlled to the at least one intermediate position to selectively pass some of the ions traveling through the single-pass drift tube into the multiple-pass drift tube while also allowing others of the ions traveling through the single-pass drift to travel through the single-pass drift tube to the outlet thereof.

In the hybrid ion mobility spectrometer of any of the first three paragraphs of this SUMMARY section, the set of ions gates may define a first combination of open and closed positions of the gates within the set of ion gates that directs ions to travel through the single-pass drift tube while blocking ions from entering the ion inlet of the multiple-pass drift tube, such that ions entering the ion inlet of the single-pass drift tube travel completely through the single-pass drift tube and exit the ion outlet thereof, a second combination of open and closed positions of the gates within the set of ion gates that directs at least some of the ions traveling through the single-pass drift tube into the ion inlet of the multiple-pass drift tube, a third combination of open and closed positions of the ion gates within the set of ion gates that directs ions in the multiple-pass drift tube to travel multiple times therethrough while blocking ions traveling through the multiple-pass drift tube from exiting the ion outlet thereof and re-entering the single-pass drift tube, and a fourth combination of open and closed positions of the ion gates within the set of ion gates that directs at least some of the ions traveling through the multiple-pass drift tube through the ion outlet thereof and into the single-pass drift tube, such that ions entering the single-pass drift tube from the ion outlet of the multiple-pass drift tube travel toward and exit through the ion outlet of the single-pass drift tube.

In the hybrid ion mobility spectrometer of any of the preceding paragraphs, the multiple-pass drift tube may comprise a closed-path drift tube, the ion inlet of the multiple-pass drift tube may comprise an ion inlet tube having an ion outlet integrally formed with the multiple-pass drift tube and the ion outlet of the multiple-pass drift tube may comprise an ion outlet tube having an ion inlet integrally formed with the multiple-pass drift tube. Illustratively, a portion of the single-pass drift tube may be integral with the closed-path drift tube. The single-pass drift tube may, for example, comprise a first plurality of cascaded drift tube segments, the closed-path drift tube may comprise a second plurality of cascaded drift tube segments with an ion outlet of a last one of the second plurality of cascaded drift tube segments coupled to an ion inlet of a first one of the second plurality of cascaded drift tube segments, and at least one of the first plurality of drift tube segments and at least one of the second plurality of drift tube segments may define at least one common drift tube segment. The ion inlet tube of the multiple-pass drift tube may have an ion inlet coupled to an ion outlet of one of the first plurality of drift tube segments of the single-pass drift tube between the ion inlet of the single-pass drift tube and the ion outlet of the single-pass drift tube, and the ion outlet tube of the multiple-pass drift tube may have an ion outlet coupled to an ion inlet of another of the first plurality of drift tube segments of the single-pass drift tube between the one of the first plurality of drift tube segments of the single-pass drift tube and the ion outlet of the single-pass drift tube. The single-pass drift tube in this embodiment is thereby defined by a cascaded arrangement of a first subset of the first plurality of drift tube segments between the ion inlet of the single-pass drift tube and the ion outlet of the one of the first plurality of drift tube segments, the ion inlet tube of the multiple-pass drift tube, at least one of the second plurality of drift tube segments of the closed-path drift tube, the ion outlet tube of the multiple-pass drift tube and at least one of the first plurality of drift tube segments between the another of the first plurality of drift tube segments and the ion outlet of the single-pass drift tube. In this embodiment, the set of ion gates may comprise a first ion gate controllable between the open position to direct ions in the multiple-pass drift tube about the closed-path drift tube and a closed position to block ions in the multiple-pass drift tube from traveling about the closed-path drift tube, and a second ion gate controllable between the closed position to block ions traveling about the closed-path drift tube from exiting the closed-path drift tube via the ion outlet tube of the multiple-pass drift tube and the open position to direct ions traveling about the closed-path drift tube through the ion outlet tube of the multiple-pass drift tube and into the single-pass drift tube. The set of ion gates may further comprise a third ion gate controllable between the open position to direct ions in the single-pass drift tube into the closed-path drift tube and a closed position to block ions in the single-pass drift tube from entering the closed-path drift tube.

In other embodiments in which the multiple-pass drift tube may comprise a closed-path drift tube, the ion inlet of the multiple-pass drift tube may comprise an ion inlet tube having an ion outlet integrally formed with the multiple-pass drift tube and the ion outlet of the multiple-pass drift tube may comprise an ion outlet tube having an ion inlet integrally formed with the multiple-pass drift tube, the single-pass drift tube may comprise a first plurality of linearly arranged, cascaded drift tube segments, the closed-path drift tube may comprise a second plurality of cascaded drift tube segments with an ion outlet of a last one of the second plurality of cascaded drift tube segments coupled to an ion inlet of a first one of the second plurality of cascaded drift tube segments, and the ion inlet of the multiple-pass drift tube may be coupled to one of the first plurality of drift tube segments and the ion outlet of the multiple-pass drift tube may be coupled to another of the first plurality of drift tube segments downstream of the one of the first plurality of drift tube segments. In this embodiment, the ion inlet tube of the multiple-pass drift tube may have an ion inlet coupled to a first ion outlet of the one of the first plurality of drift tube segments of the single-pass drift tube, the one of the first plurality of drift tube segments of the single-pass drift tube may have a second ion outlet coupled to an ion inlet of a next one of the first plurality of drift tube segments, the ion outlet tube of the multiple-pass drift tube may have an ion outlet coupled to a first ion inlet of the another of the first plurality of drift tube segments of the single-pass drift tube, and the another of the first plurality of drift tube segments may have a second ion inlet coupled to an ion outlet of a previous one of the first plurality of drift tube segments that is downstream of the next one of the first plurality of drift tube segments. Further in this embodiment, the set of ion gates may comprise a first ion gate controllable between the open position to direct ions in the one of the first plurality of drift tube segments of the single-pass drift tube through the first ion outlet thereof and into the ion inlet tube of the multiple-pass drift tube and the closed position to block ions in the one of the first plurality of drift tube segments of the single-pass drift tube from passing through the first ion outlet thereof and entering the ion inlet tube of the multiple-pass drift tube, and a second ion gate controllable between the open position to direct ions in the one of the first plurality of drift tube segments of the single-pass drift tube through the second ion outlet thereof and into the ion inlet of the next one of the first plurality of drift tube segments and the closed position to block ions in the one of the first plurality of drift tube segments of the single-pass drift tube from passing through the second ion outlet thereof and entering the ion inlet of the next one of the first plurality of drift tube segments. The set of ion gates in this embodiment may further comprise a third ion gate controllable between the open position to direct ions in the multiple-pass drift tube about the closed-path drift tube and a closed position to block ions in the multiple-pass drift tube from traveling about the closed-path drift tube, and a fourth ion gate controllable between the closed position to block ions traveling about the closed-path drift tube from exiting the closed-path drift tube via the ion outlet tube of the multiple-pass drift tube and the open position to direct ions traveling about the closed-path drift tube through the ion outlet tube of the multiple-pass drift tube and into the single-pass drift tube.

In the hybrid ion mobility spectrometer of any of the first four paragraphs of this SUMMARY section, the single-pass drift tube may alternatively comprise a first plurality of linearly arranged, cascaded drift tube segments, the multiple-pass drift tube may comprise a closed-path drift tube, with the closed-path drift tube comprising a second plurality of cascaded drift tube segments with an ion outlet of a last one of the second plurality of cascaded drift tube segments coupled to an ion inlet of a first one of the second plurality of cascaded drift tube segments, and the ion inlet and the ion outlet of the multiple-pass drift tube may together comprise an ion inlet-outlet tube coupled at one end to one of the first plurality of drift tube segments between the ion inlet of the single-pass drift tube and the ion outlet of the single-pass drift tube and at an opposite end to one of the second plurality of drift tube segments. The set of ion gates in this embodiment may comprise a first ion gate controllable between the open position to direct ions in the one of the first plurality of drift tube segments of the single-pass drift tube therethrough and into an ion inlet of a next one of the first plurality of drift tube segments and the closed position to block ions in the one of the first plurality of drift tube segments of the single-pass drift tube from passing therethrough and entering the ion inlet of the next one of the first plurality of drift tube segments, and a second ion gate controllable between the open position to direct ions in the one of the first plurality of drift tube segments therethrough and into the ion inlet-outlet tube or to direct ions in the ion inlet-outlet tube therethrough and into the one of the first plurality of drift tube segments, and a closed position to block ions in the first one of the plurality of drift tube segments from passing therethrough and entering the ion inlet-outlet tube or to block ions in the ion inlet-outlet tube from passing therethrough and entering the one of the first plurality of drift tube segments. The set of ion gates may further comprise a third ion gate controllable between the open position to direct ions in the ion inlet-outlet tube therethrough and into the closed-path drift tube or to direct ions in the closed-path drift tube therethrough and into the ion inlet-outlet tube, and the closed position to block ions in the ion inlet-outlet tube from passing therethrough and entering the closed-path drift tube or to block ions in the closed-path drift tube from passing therethrough and entering the ion inlet-outlet tube, and a fourth ion gate controllable between the open position to direct ions in the multiple-pass drift tube about the closed-path drift tube and a closed position to block ions in the multiple-pass drift tube from traveling about the closed-path drift tube.

The hybrid ion mobility spectrometer of any of the preceding paragraphs may further comprise an ion source coupled to the ion inlet of the single-pass drift tube, the ion source configured to generate ions from a sample.

The hybrid ion mobility spectrometer of any of the preceding paragraphs may further comprise an ion detector to detect ions exiting the ion outlet of the single-pass drift tube and to produce an ion detection signal corresponding thereto. The hybrid ion mobility spectrometer in this embodiment may further comprise a processor to process the ion detection signal and produce corresponding ion mobility spectral information as a function of ion drift time.

A method for separating ions may comprise introducing ions into an ion inlet of a first drift tube, establishing at least a first electric field within the first drift tube to cause the ions introduced into the ion inlet thereof to travel through the first drift tube from the ion inlet thereof toward an ion outlet thereof while separating in time according to a first function of ion mobility, controlling a set of ion gates to direct at least some of the ions traveling through the first drift tube into a second drift tube via an ion inlet of the second drift tube that is coupled to the first drift tube between the ion inlet of the first drift tube and the ion outlet of the first drift tube, establishing at least a second electric field within the second drift tube to cause ions entering the ion inlet thereof to travel through the second drift tube while separating in time according to the first or a second function of ion mobility, controlling the set of ion gates to cause ions traveling through the second drift tube to travel through the second drift tube multiple times, and controlling the set of ion gates to direct at least some of the ions having traveled the multiple times through the second drift tube into the first drift tube via an ion outlet of the second drift tube that is coupled to the first drift tube between the ion inlet of the first drift tube and the ion outlet of the first drift tube, wherein at least some of the ions passing into the first drift tube from the ion outlet of the second drift tube travel toward and exit through the ion outlet of the first drift tube.

Introducing ions into the ion inlet of the first drift tube may comprise introducing a first set of ions into the ion inlet of the first drift tube, and the method may further comprise controlling the set of ion gates to cause the first set of ions to travel through the first drift tube and exit through the ion outlet the first drift tube, determining, based on the first set of ions exiting the ion outlet of the first drift tube, a range of ion mobilities of at least some of the first set of ions, and introducing a second set of ions into the ion inlet of the first drift tube after introducing the first set of ions into the ion inlet of the first drift tube. Controlling the set of ion gates to direct at least some of the ions traveling through the first drift tube into the second drift tube in this embodiment may comprise controlling the set of ion gates to direct the second set of ions traveling through first drift tube into the second drift tube via the ion inlet of the second drift tube, and the method may further comprise controlling the second electric field to cause only ions in the second set of ions that are within the determined range of ion mobilities to travel through the second drift tube. Controlling the set of ion gates to direct at least some of the ions having traveled the multiple times through the second drift tube into the first drift tube may then illustratively comprise controlling the set of ion gates to direct ions from the second set of ions that are traveling through the second drift tube into the first drift tube via the ion outlet of the second drift tube, and the ions from the second set of ions passing into the first drift tube from the ion outlet of the second drift tube may exit through the ion outlet of the first drift tube and have ion mobilities only within the determined range of ion mobilities. The method may further comprise generating the first and second sets of ions from a common sample.

The second drift tube may comprise a number of cascaded drift tube segments, and controlling the second electric field to cause only ions in the second set of ions that are within the range of ion mobilities to travel through the second drift tube may comprise sequentially establishing and disestablishing the second electric field within the cascaded drift tube segments at a rate that corresponds to drift times associated with the range of ion mobilities.

The second drift tube may define a closed path, the ion inlet of the second drift tube comprises an ion inlet tube integrally formed with the second drift tube and the ion outlet of the second drift tube comprises an ion outlet tube also integrally formed with the second drift tube, and controlling the set of ion gates to cause ions traveling through the second drift tube to travel through the second drift tube multiple times may comprise controlling the set of ion gates to block the ions traveling through the second drift tube from exiting the second drift tube via the ion outlet of the second drift tube and to direct the ions traveling through the second drift tube to travel multiple times about the closed path.

One or more of the steps of controlling the set of ion gates may comprise controlling the set of ion gates using a processor.

An ion detector may detect ions exiting the ion outlet of the first drift tube and produce an ion detection signal corresponding thereto, and the method may further comprise processing the ion detection signal to produce ion mobility spectral information as a function of ion drift time.

The method may further comprise generating ions prior to introducing the ions into the ion inlet of the first drift tube.

The method may further comprise clearing the first drift tube of ions after introducing the first set of ions into the ion inlet of the first drift tube and before introducing the second set of ions into the ion inlet of the second drift tube.

A plurality of voltage sources may each be operatively connected to one or more of the ion gates in the set of ion gates, and each of the ion gates in the set of ion gates may be controllable between an open position to pass ions therethrough and a closed position to block ions from passing therethrough. Each of the ion gates in the set of ions gates may be responsive to a first voltage applied thereto to open to the open position and to a second voltage applied thereto to close to the closed position. One or more of the steps of controlling the set of ion gates may comprise controlling voltages produced by one or more of the plurality of voltage sources to selectively control one or more of the ion gates in the set of ion gates to the open or closed position. The voltage produced by the one or more of the plurality of voltage sources may be programmable, wherein controlling voltages produced by the one or more of the plurality of voltage sources may comprise programming the one or more of the plurality of voltage sources to control the timing of production of the first and/or second voltages, or a processor may be operatively connected to the one or more of the plurality of voltage sources, and controlling voltages produced by the one or more of the plurality of voltage sources may comprise controlling via the processor the timing of production of the first and/or second voltages.

Controlling the set of ion gates to direct at least some of the ions traveling through the first drift tube into the second drift tube may, in some embodiments, comprise controlling the set of ion gates to direct some of the ions traveling through the first drift tube into the second drift tube while also allowing others of the ions traveling through the first drift to travel through the first drift tube to the outlet thereof. In such embodiments, introducing ions into the ion inlet of the first drift tube may comprise continually introducing ions into the ion inlet of the first drift tube. Alternatively, introducing ions into the ion inlet of the first drift tube may comprise intermittently or periodically introducing ions into the ion inlet of the first drift tube.

DESCRIPTION OF THE ILLUSTRATIVE EMBODIMENTS

For the purposes of promoting an understanding of the principles of the invention, reference will now be made to a number of illustrative embodiments shown in the attached drawing and specific language will be used to describe the same.

Figure 1A:
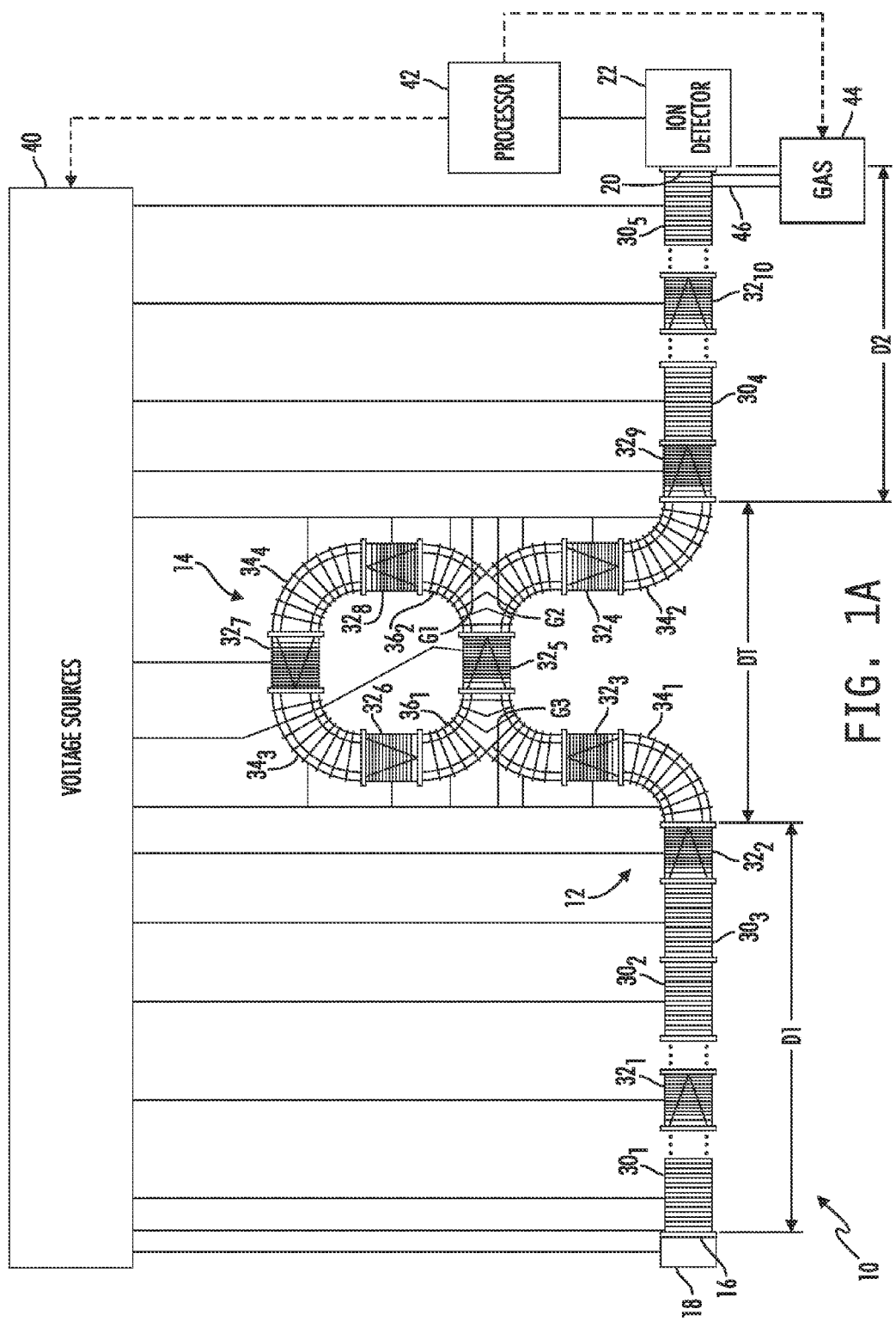
FIG. 1A is a simplified diagram of an embodiment of a hybrid ion mobility spectrometer.

Referring to FIG. 1A, a simplified diagram of an embodiment of a hybrid mobility spectrometer 10 is shown. The hybrid ion mobility spectrometer 10 illustratively includes a single-pass drift tube 12 through which ions can be separated in time according to a first function of ion mobility, and a multiple-pass drift tube 14, coupled to the single-pass drift tube 12 between an ion inlet 16 and an ion outlet 20 of the single-pass drift tube 12, through which ions can be separated in time according to a second function of ion mobility. The spectrometer 10 further illustratively includes a set of ion gates, e.g., G1-G3, each of which are controllable between open and closed positions, and the set of ion gates is illustratively controlled such that some or all of the ions traveling through the single-pass drift tube 12 may be selectively passed into the multiple-pass drift tube 14 via an ion inlet $36_1$ of the multiple-pass drift tube 14, and some or all of the ions traveling through the multiple-pass drift tube 14 may be selectively passed back into the single-pass drift tube 12 via an ion outlet $36_2$ of the multiple-pass drift tube 14, and the ions then exit the single-pass drift tube 12 via the ion outlet 20 thereof. In the embodiment illustrated in FIG. 1A, an ion source 18 is coupled to the ion inlet 16 of the single-pass drift tube 12, and an ion detector 22 is positioned to receive ions exiting the ion outlet 20 of the single-pass drift tube 12.

The foregoing configuration of the ion mobility spectrometer 10 provides for the ability to pass all or a subset of ions in the single-pass drift tube 12 to the multiple-pass drift tube 14 for additional and/or alternate separation before the ions exit the outlet 20 of the single-pass drift tube 12. Advantageously, because both drift tubes 12, 14 operate on ions generated from a single ion source 18 coupled to the ion inlet 16 of the single-pass drift tube 12, such additional and/or alternate separation may thus be carried out using ions from the same sample. In one specific operational mode of the hybrid ion mobility spectrometer 10 illustrated in FIG. 1A, for example, the set of ion gates, e.g., ion gates G1-G3, may be controlled such that ions generated by the ion source 18 are first confined to the single-pass drift tube 12, and electric fields within the single-pass drift tube 12 are controlled such that ions generated at the ion source 18 travel, i.e., drift, through only the single-pass drift tube 12 where they separate in time as a first function of ion mobility defined by the various structural dimensions and operating parameters of the single-pass drift tube 12. The resulting ion spectral information is then analyzed and if, for example, it is discovered that in the ion spectral information a subset, e.g., two or more, of ion intensity peaks in an ion mobility range of interest, e.g., in a particular range of drift times, are crowded together and cannot be satisfactorily resolved over the length of the single-pass drift tube 12, ions are then generated a second time, or are continuously generated without interruption, and the set of ion gates, e.g., ion gates G1-G3, is controlled in one embodiment to pass or divert ions traveling through the single-pass drift tube 12 that are within the ion mobility range of interest into the multiple-pass drift tube 14. The set of ion gates, e.g., ion gates G1-G3, is then controlled to confine the diverted ions within the multiple-pass drift tube 14 and electric fields within the multiple-pass drift tube 14 are controlled such that the diverted ions pass, i.e., drift, one or more times through, i.e., about, the multiple-pass drift tube 14 and separate in time according to a second function of ion mobility, which may or may not be the same as the first function of ion mobility, and which is defined by the structure and operating parameters of the multiple-pass drift tube 14, and the set of ion gates, e.g., ion gates G1-G3 may then be controlled to pass or divert some or all of the ions traveling through the multiple-pass drift tube 14 back into the single-pass drift tube 12 where they are then directed to the ion outlet 20 of the single-pass drift tube. In one alternate embodiment, the set of ion gates, e.g., ion gates G1-G3, may be controlled to pass or divert ions some or all of the ions traveling through the single-pass drift tube 12 into the multiple-pass drift tube 14, and the electric fields within the multiple-pass drift tube 14, along with the set of ion gates, e.g., ion gates G1-G3, may then controlled in a known manner to confine the diverted ions within the multiple-pass drift tube 14 so that the ions separate in time according to a second function of ion mobility in which only the diverted ions within the ion mobility range of interest pass one or more times through, i.e., about, the multiple-pass drift tube 14. The set of ion gates, e.g., ion gates G1-G3 may then be controlled to pass or divert some or all of the ions traveling through the multiple-pass drift tube 14 back into the single-pass drift tube 12 where they are then directed to the ion outlet 20 of the single-pass drift tube. In another alternate embodiment, the set of ion gates, e.g., ion gates G1-G3, may be controlled to pass or divert some or all of the ions traveling through the single-pass drift tube 12 into the multiple-pass drift tube 14, and the electric fields within the multiple-pass drift tube 14, along with the set of ion gates, e.g., ion gates G1-G3, may then controlled in a known manner to confine the diverted ions within the multiple-pass drift tube 14 so that the ions separate in time according to a second function of ion mobility, which may or may not be the same as the first function of ion mobility, and which is defined by the structure and operating parameters of the multiple-pass drift tube 14. The ion gates, e.g., ion gates G1-G3, may then be controlled to pass or divert some or all of the ions traveling through the multiple-pass drift tube 14 back into the single-pass drift tube 12, and one or more ion gates positioned within the drift tube section D2 may be controlled to pass through the ion outlet 20 only ions within the ion mobility range of interest.

In some embodiments, one or more of the ion gates in the set of ion gates, e.g., G1-G3, may be controlled to one or more intermediate positions between the open and closed positions. In such embodiments, and according to another specific operating mode of the hybrid ion mobility spectrometer 10 illustrated in FIG. 1A, for example, the set of ion gates, e.g., ion gates G1-G3, may be controlled to direct some of the ions traveling through the single-pass drift 12 into the multiple-pass drift tube 14 while also allowing others of the ions traveling through the single-pass drift tube 12 to travel completely through the single-pass drift tube 12, e.g., to and through the outlet 20 thereof. In such an operating mode, ions supplied by the single or common ion source 18 to the inlet 16 of the single-pass drift tube 12 thus travel in parallel through the single-pass drift tube 12 and the combination of the single-pass drift tube 12 and the multiple-pass drift tube 14, with some of the ions traveling directly through the single-pass drift tube 12 to and through the ion outlet 20 and others of the ions traveling through the single-pass drift tube 12, to and through the multiple-pass drift tube 14, then back to and through any remaining section(s) of the single-pass drift tube 12 and exiting the ion outlet 20 of the single-pass drift tube 12.

In any case, further details relating to various structural embodiments of the hybrid ion mobility spectrometer briefly described above and the foregoing operation thereof are described below and/or illustrated in the attached drawings, although it will be understood that other structural embodiments and operational modes of the hybrid ion mobility spectrometer illustrated and described herein will occur to those skilled in the art and that such other structural embodiments and operational modes are contemplated by this disclosure.

Referring now specifically to FIG. 1A, an embodiment of the hybrid ion mobility spectrometer 10 briefly described above is shown. As described above, the hybrid ion mobility spectrometer 10 includes an ion source 18 coupled to an ion inlet 16 defined at one end of a single-pass ion mobility spectrometer 12, and an ion outlet 20 is defined at an opposite end of the single-pass ion mobility spectrometer 12. A multiple-pass ion mobility spectrometer 14 is coupled to the single-pass ion mobility spectrometer 12 between the ion inlet 16 and the ion outlet 20 thereof such that ions may be selectively passed from the single-pass ion mobility spectrometer 12 to the multiple-pass ion mobility spectrometer 14 and vice versa. For purposes of this disclosure, the term "single-pass ion mobility spectrometer" means an ion mobility spectrometer, or portion thereof, through which ions pass a single time, and the term "multiple-pass ion mobility spectrometer" means an ion mobility spectrometer, or portion thereof, through which ions may pass multiple times. Neither such ion mobility spectrometer is limited to any particular shape or configuration, and the single-pass ion mobility spectrometer 12 and/or the multiple-pass ion mobility spectrometer 14 may be or include a linear, piece-wise-linear and/or non-linear drift tube.

In the illustrated embodiment, the ion outlet 20 of the single-pass ion mobility spectrometer 12 is coupled to an ion detector 22 which is configured to detect, in a conventional manner, ions exiting the ion outlet 20 of the single-pass ion mobility spectrometer 12. In alternate embodiments, one or more additional ion separation and/or ion analyzing apparatuses may be positioned between the ion outlet 20 of the single-pass ion mobility spectrometer 12 and the ion detector 22, and in any such alternate embodiment one or more ion detectors 22 may be coupled to or integral with any of the additional ion separation and/or ion analyzing apparatuses, alternatively to or in addition to the single-pass ion mobility spectrometer 12.

The ion source 18 may be any conventional ion source, examples of which include, but are not limited to, an electrospray ion source, a matrix-assisted laser desorption ion source (MALDI), or the like. Alternatively or additionally, the ion source 18 may include one or more conventional apparatuses to collect all or a subset of the generated ions (i.e., within a defined range of ion mobilities and/or within a defined range of ion mass-to-charge ratios) and/or to structurally modify, e.g., fragment and/or change the conformations of, some or all of the generated ions and/or to normalize or otherwise modify the charge states of one or more of the generated ions. Alternatively or additionally still, the ion source 18 may be or include one or more known apparatuses that separate ions and/or one or more isotopes thereof as a function of any molecular characteristic, e.g., ion mass-to-charge ratio, ion mobility, ion retention time, or the like.

In the embodiment illustrated in FIG. 1A, the single-pass ion mobility spectrometer 12 is made up of three cascaded drift tube sections; a first drift tube section D1 coupled to the ion source 18, a transition drift tube section DT coupled to the first drift tube section D1 and to the drift tube of the multiple-pass ion mobility spectrometer 14, and a second drift tube section D2 coupled to the transition drift tube section DT and, in the illustrated embodiment, to the ion detector 22. In one embodiment, the first drift tube section D1 is illustratively a linear drift tube section and includes a cascaded arrangement of any number, N, of conventional linear drift tube sub-sections $30_N$ (three such drift tube sub-sections $30_1$, $30_2$ and $30_3$ shown) and any number, M, of conventional linear drift tube funnels $32_M$ (two such drift tube funnels $32_1$ and $32_2$ shown), wherein a different drift tube funnel 32 may be interposed between any number of cascaded drift tube sub-sections 30. The second drift tube section D2 is likewise illustratively a linear drift tube section and may likewise include a cascaded arrangement of any number, Q, of conventional drift tube sections $30_Q$ (two such drift tube sub-sections $30_4$ and $30_5$ shown) and any number, R, of conventional drift tube funnels $32_R$ (two such drift tube funnels $32_9$ and $32_{10}$ shown), wherein a different drift tube funnel 32 may be interposed between any number of cascaded drift tube sub-sections 30. Alternatively, the second drift tube section D2 may include only a single drift tube sub-section 30 or drift tube funnel 32 which is coupled at one end to the transition drift tube section DT and defines the ion outlet 20 of the single-pass ion mobility spectrometer 12 at its opposite end. Alternatively still, the second drift tube section D2 may be omitted altogether and the ion outlet of the transition drift tube section DT may define the ion outlet 20 of the single-pass ion mobility spectrometer 12.

The drift tube sub-sections 30 and the drift tube funnels 32 illustrated in FIG. 1A are illustratively linear components in that each drift tube sub-section 30 and each drift tube funnel 32 defines a linear ion drift tube axis therethrough between an ion inlet and ion outlet thereof. The resulting drift tube sections D1 and D2 shown in FIG. 1A therefore likewise linear drift tube sections, it will be understood that either or both of the drift tube sections D1 and D2 may alternatively be piecewise linear or non-linear, or include one or more piecewise linear or non-linear subsections.

In any case, the one or more drift tube funnels 32 are illustratively controlled in a conventional manner to radially focus ions inwardly toward a central ion drift axis defined through the drift tube funnel 32 from an ion inlet to an ion outlet thereof. Additionally, one or more of the ion funnels 32 and/or one or more of the drift tube sub-sections 30 may include one or more ion gates controllable in a conventional manner to selectively pass ions therethrough or block ions from passing therethrough. Alternatively or additionally, one or more of the ion funnels 32 may include one or more regions that is/are controllable in a conventional manner to modify the structures of some or all of the ions passing therethrough, e.g., via ion fragmentation and/or inducing conformational changes in the ions. Further details relating to illustrative embodiments of the drift tube sub-sections 30 and the drift tube funnels 32 shown in FIG. 1A and described above are described in U.S. Patent Pub. No. 2007/0114382 A1 and also in related U.S. Pat. No. 8,618,475, the disclosures of which are incorporated herein by reference.

The transition drift tube section DT in the embodiment illustrated in FIG. 1A, is illustratively made up of a number, S, of curved drift tube sub-sections $34_S$ (two such curved drift tube sub-sections $34_1$ and $34_2$ shown, with the curved drift tube sub-section $34_1$ defining an ion inlet to the transition drift tube section DT and coupled to the ion outlet of the first drift tube section D1, and with the curved drift tube sub-section $34_2$ defining an ion outlet of the transition drift tube section DT and coupled to the ion inlet of the second drift tube section D2), a number, T, of the drift tube funnels $32_T$ (three such drift tube funnels $32_3$, $32_4$ and $32_5$ shown) and sub-sections of each of two curved, Y-shaped drift tube sections $36_1$ and $36_2$. The multiple-pass ion mobility spectrometer 14, in the embodiment illustrated in FIG. 1A, is illustratively provided in the form of a closed-path drift tube made up of a number, U, of the curved drift tube sub-sections $34_U$ (two such curved drift tube sub-sections $34_3$ and $34_4$ shown), remaining sub-sections of the two curved, Y-shaped drift tube sections $36_1$ and $36_2$, and a number, V, of the drift tube funnels $32_V$ (four such drift tube funnels $32_5$, $32_6$, $32_7$ and $32_8$ shown). It will be understood, however, that the multiple-pass drift tube 14 may alternatively not form a closed path but may nevertheless be configured to pass ions multiple times therethrough.

In the embodiment illustrated in FIG. 1A, the sub-section or branch of the curved, Y-shaped drift tube section $36_1$ that is coupled to the drift tube funnel $32_3$ serves the dual function as part of the single-pass ion mobility spectrometer 12 and also as an ion inlet to the multiple-pass ion mobility spectrometer 14, and the sub-section or branch of the curved, Y-shaped drift tube section $36_2$ that is coupled to the drift tube funnel $32_4$ likewise serves the dual function as part of the single-pass ion mobility spectrometer 12 and also as an ion outlet of the multiple-pass ion mobility spectrometer 14. The drift tube funnel $32_5$ is illustratively shared by the single-pass ion mobility spectrometer 12 and the multiple-pass ion mobility spectrometer 14 and therefore forms part of each. Further details relating to illustrative embodiments of the curved drift tube sub-sections 34, the curved Y-shaped drift tube sections 36 and the closed-path configuration of the multiple-pass ion mobility spectrometer 14 shown in FIG. 1A and described above are described in U.S. Pat. No. 8,362,420, the disclosure of which is incorporated herein by reference.

The hybrid ion mobility spectrometer 10 illustrated in FIG. 1A includes three ion gates, G1-G3, each of which is controllable in a conventional manner to selectively allow ions to pass therethrough and to selectively block ions from passing therethrough. In one embodiment, the ion gates G1-G3 are each provided in the form of a mesh or grid, and a DC potential applied thereto, or a DC differential applied between a mesh or grid and an adjacent ring, is controlled such that at one DC level or DC differential value ions pass through the ion gate and at a different DC level or DC differential value ions are blocked from passing through the ion gate. In alternate embodiments, the ion gate function of one or more of the ion gates G1-G3 may be accomplished by selectively applying and varying the frequency and/or amplitude of an RF voltage to a non-meshed or gridded ring, in a conventional manner, to selectively allow passage or block passage of ions therethrough. In some embodiments, one or more of the gates G1-G3 may be controlled with intermediate DC potentials and/or RF frequencies/amplitudes to pass therethrough only a portion of ions presented thereat, e.g., to allow passage through one or more of the ion gates G1-G3 of only a percentage of ions that is less than 100% of the total number of ions traveling toward the one or more ion gates G1-G3. In any case, the three ion gates G1-G3 are controllable, as will be described in detail below, to confine ions within the single-pass drift tube 12, to confine ions within the multiple-pass drift tube 14, to pass or divert at least some of the ions in the single-pass drift tube 12 into the multiple-pass drift tube 14 and/or to pass or divert at least some of the ions in the multiple-pass drift tube 14 back into the single-pass drift tube 12.

In the embodiment illustrated in FIG. 1A, a first one of the ion gates, G1, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_8$. A second one of the ion gates, G2, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_4$. A third one of the ion gate, G3, is illustratively positioned in the curved, Y-shaped drift tube section $36_1$ at an interface of the sub-section of the Y-shaped drift tube section $36_1$ that is coupled to the drift tube funnel $32_5$ and the sub-section or branch of the Y-shaped drift tube section $36_1$ that is coupled to the drift tube funnel $32_3$. It will be understood that the hybrid ion mobility spectrometer 10 may include more or fewer such ion gates, and that any such alternative embodiment of the hybrid ion mobility spectrometer is contemplated by this disclosure.

In one alternate embodiment of the hybrid ion mobility spectrometer 10, one or more of the drift tube sub-sections 30, 34, 36 and/or one or more of the drift tube funnels 32 may be provided in the form of a two-part sub-section or funnel defining a first drift tube region having an ion inlet defining the ion inlet of the sub-section or funnel and an ion outlet coupled to an ion inlet of an ion elimination region having an ion outlet defining the ion outlet of the sub-section or funnel. Further details relating to the structure and various operational modes of such alternately configured drift tube sub-sections and/or funnels are described in co-pending U.S. Patent Application Pub. No. 2013/0292562, the disclosure of which is incorporated herein by reference.

Figure 2:
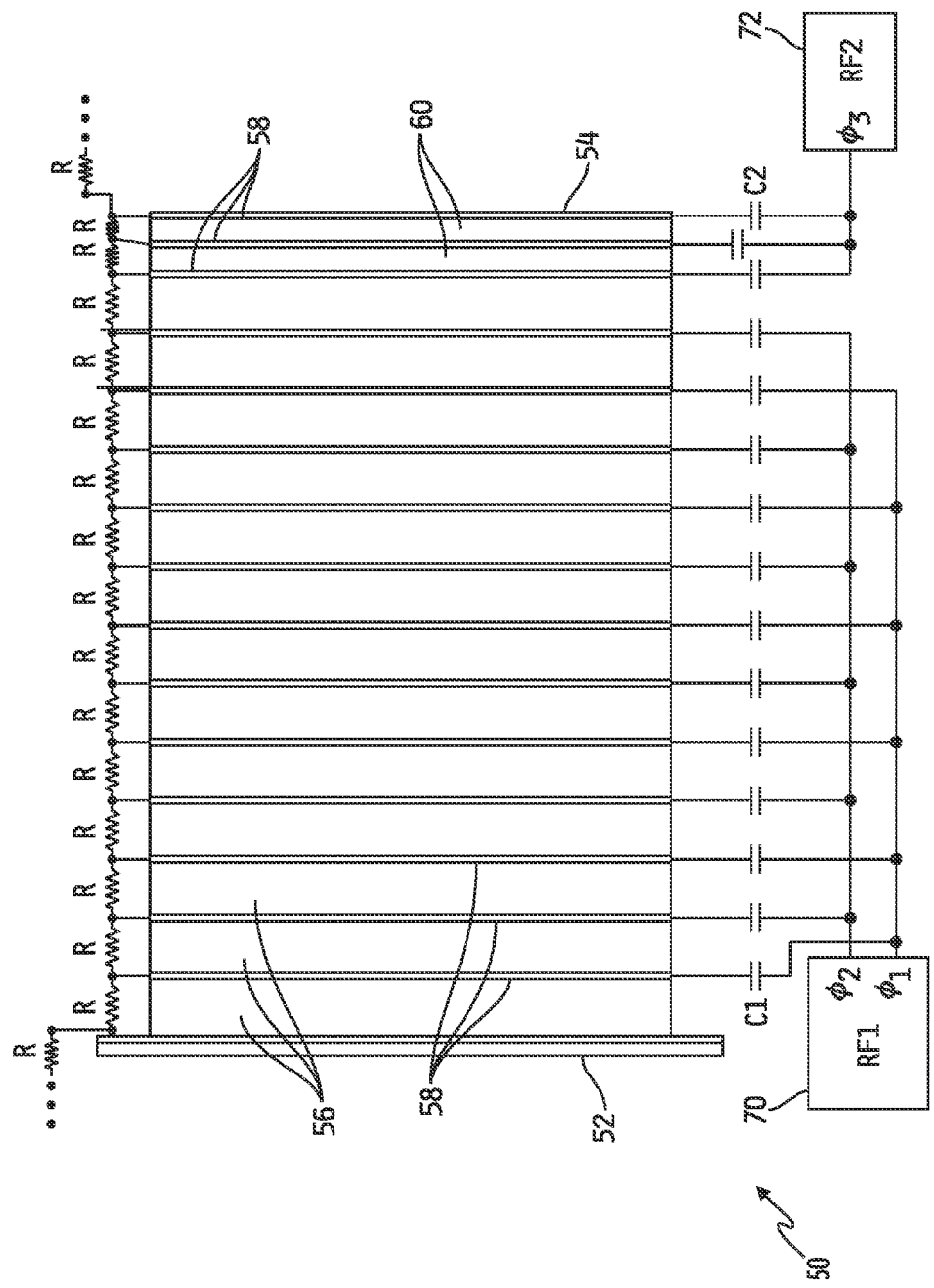
FIG. 2 is a simplified diagram of an embodiment of a drift tube segment that may be used in any of the hybrid ion mobility spectrometers of FIGS. 1A-1C.

In another alternate embodiment of the hybrid ion mobility spectrometer 10, one or more of the drift tube funnels 32 and/or one or more of the drift tube sub-sections 30, 34, 36 may be provided in the form of a conventional drift tube sub-section 30 to which RF voltages may be applied to radially focus ions inwardly toward the ion drift path defined therethrough. One illustrative embodiment of such a drift tube sub-section 50 is shown in FIG. 2, and includes a series of identically-dimensioned, electrically insulating rings 56 each separating adjacent ones of a series of identically-dimensioned, electrically conductive rings 58, with all such rings 56, 58 stacked and clamped together between an ion inlet 52 and an ion outlet 54 of the drift tube sub-section 50. Illustratively, the last several, e.g., two, electrically insulating rings may be (but need not be) provided in the form of reduced-thickness rings 60 (e.g., approximately ½ of the thickness of the rings 56), the purpose which will be described below.

In the illustrated embodiment, an RF voltage source 70 produces two RF voltages, $\phi_1$ and $\phi_2$ each 180 degrees out of phase with respect to the other, with $\phi_1$ applied via a separate capacitor, C1, to all odd (or even) numbered rings 58 and $\phi_2$ applied via a separate capacitor, C1, to all even (or odd) numbered rings 58 such that $\phi_1$ and $\phi_2$ are applied alternately to the series of rings 58 in the stack. A DC potential is applied via series-connected resistors, R, to the rings 58 to create a substantially uniform electric drift field in the drift tube sub-section 50, and ions drift through the drift tube sub-section 50 under the influence of the electric drift field. The frequencies and/or amplitudes of the RF voltages $\phi_1$ and $\phi_2$ are illustratively selected in a conventional manner to radially focus ions drifting through the drift tube sub-section 50 toward an ion drift axis defined centrally through the drift tube sub-section 50. In embodiments in which the reduced-width, electrically insulating rings 60 are included, another RF voltage source 72 may be provided to produce an RF voltage $\phi_3$ that is applied through a different capacitor, C2, to each of the electrically conductive rings 58 contacting one of the rings 60. The frequency and/or amplitude of $\phi_3$ is controlled in a conventional manner to selectively allow passage of ions through the electrically conductive rings 58 connected to $\phi_3$ or block passage of ions therethrough to thereby provide an ion gating function.

The drift tube sub-sections 50 with the radial ion focusing feature described above may be used in place of one or more of the drift tube funnels 32 and/or in place of one or more of the drift tube sub-sections 30, 34, 36 illustrated in FIG. 1A. Alternatively or additionally, the drift tube sub-sections 50 with or without the radial ion focusing feature but with the ion gating feature described above may be used in place of one or more of the ion gates G1-G3 illustrated in FIG. 1A. In any of the embodiments illustrated in the attached figures and described herein, either or both of the single-pass drift tube and the multiple-pass drift tube may be operated in a conventional traveling wave operating mode, i.e., one in which one or more oscillating, i.e., AC, electric fields are established within the various drift tube sections to cause the ions to separate as they drift through the respective drift tube.

Referring again to FIG. 1A, a number of voltage sources 40 are electrically connected to various parts of the hybrid ion mobility spectrometer 10, and the number of voltage sources 40 are selected and controlled to apply appropriate DC and/or AC voltages to the various parts and components of the hybrid ion mobility spectrometer 10 for operation thereof. For example, one or more of the voltage sources 40 is/are electrically connected to the ion source 18 to control the ion source 18 in a conventional manner to generate, collect and/or process ions as described above. One or more others of the voltage sources 40 is/are electrically connected to each drift tube sub-section 30, 34, 36 and each drift tube funnel 32 to establish an electric drift field therein through which ions traverse the single-pass drift tube 12 and the multiple-pass drift tube 14. One or more others of the voltage sources 40 is/are electrically connected to the drift tube funnels 32 to radially focus ions inwardly toward the drift tube axis defined therethrough, and/or to control operation of one or more ion gates contained therein to pass or block ions, and/or to control one or more ion activation regions included in one or more of the funnels 32 to modify the structure of ions passing therethrough, e.g., via ion fragmentation and/or by inducing conformational changes in ions without fragmenting them. One or more others of the voltage sources 40 is/are electrically connected to each of the ion gates G1-G3 and selectively controlled to pass or block ions as described above and as will be described in greater detail below with respect to the process illustrated in FIG. 3. In any case, the one or more voltage sources 40 are conventional and may be individually programmed for operation or controlled by a processor 42 (e.g., amplitude, frequency, timing of activation and/or deactivation, etc.) as shown by dashed-line representation. The processor 42 is, in any event, electrically connected to the ion detector, and the processor 42 includes a memory having instructions stored therein that are executable by the processor 42 to process ion detection signals produced by the ion detector 22 and produce corresponding ion mobility spectral information, e.g., as a function of ion drift time through the single-pass drift tube 12 and/or the multiple-pass drift tube 14.

A gas source 44, e.g., single buffer gas, combination of gases to form a buffer gas, one or a combination of other gases, etc., is fluidly coupled to the hybrid ion mobility spectrometer 10 via a fluid conduit 46. In embodiments of the hybrid ion mobility spectrometer 10 constructed from open-ended sub-sections 30, 34, 36 and with or without open-ended drift tube funnels 32, the resulting spectrometer 10 is a continuous cavity spectrometer, and the single gas source 44 may thus be used to fill the entire spectrometer 10, including the single-pass drift tube 12 and the multiple-pass drift tube 14. In alternative embodiments, two or more gas sources may be used, and the hybrid ion mobility spectrometer 10 may be partitioned in a conventional manner to confine the two or more gases to corresponding portions of the spectrometer 10. The gas source 44 may be manually controlled, programmable for automatic control and/or controlled by the processor 42 as shown by dashed-line representation in FIG. 1A.

Figure 1B:
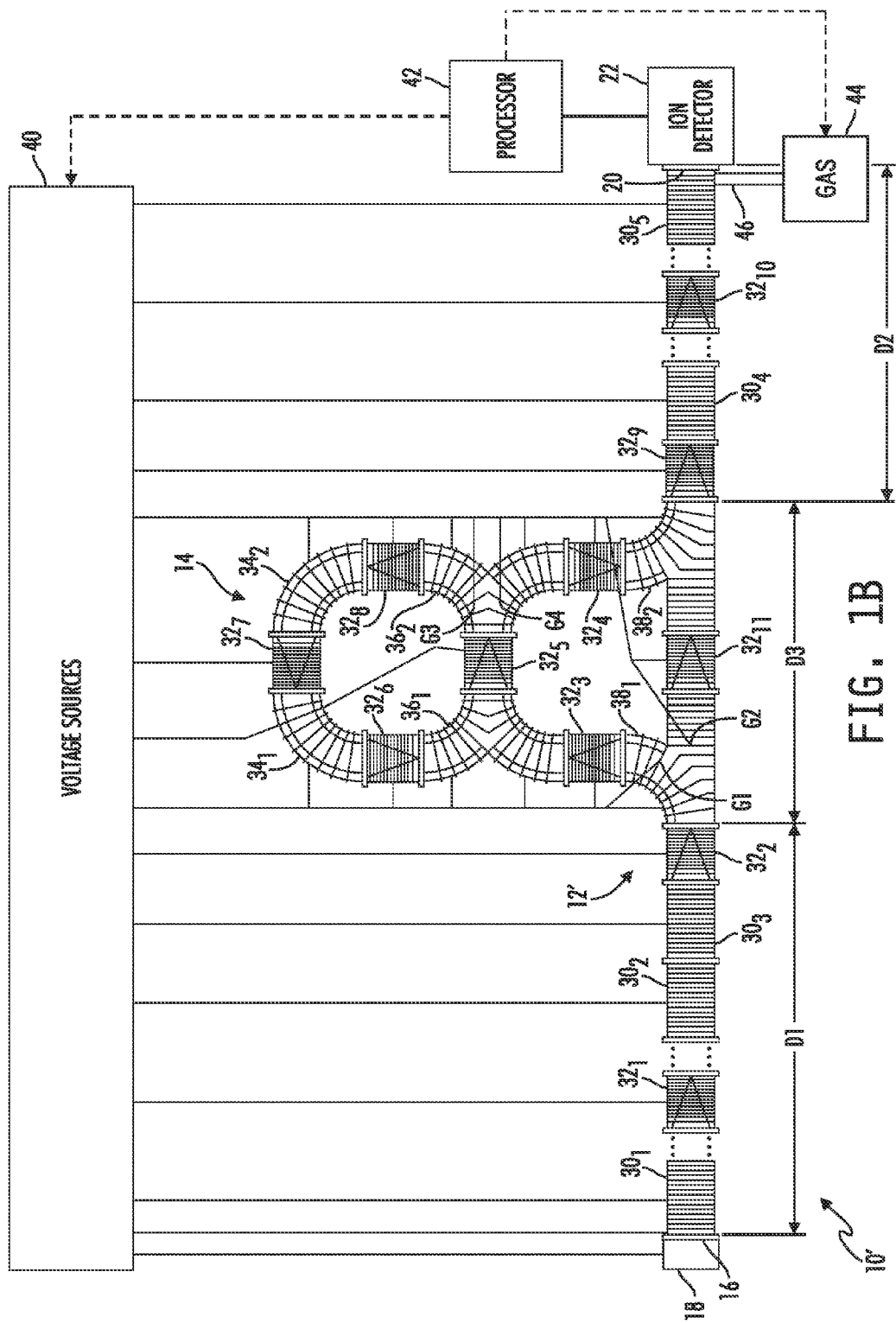
FIG. 1B is a simplified diagram of an alternate embodiment of a hybrid ion mobility spectrometer.

Referring now to FIG. 1B, an alternate embodiment of a hybrid ion mobility spectrometer 10' is shown. The hybrid ion mobility spectrometer 10' is identical in many respects to the hybrid ion mobility spectrometer 10 illustrated in FIG. 1A and described above. Like features are identified by like reference numbers, and a detailed description of common features between the two spectrometers 10 and 10' will not be repeated here for brevity. It will be further understood that the various embodiments of the various components and aspects to the hybrid ion mobility spectrometer 10 described above apply equally to the hybrid ion mobility spectrometer 10'.

The hybrid ion mobility spectrometer 10' illustrated in FIG. 1B differs from the hybrid ion mobility spectrometer 10 illustrated in FIG. 1A primarily in the construction of the single-pass drift tube 12' and in the number and location of the various ion gates that are controlled to achieve operation of the spectrometer 10 as described above. In the embodiment illustrated in FIG. 1B, for example, the drift tube funnel $32_3$ is coupled at its ion inlet to one ion outlet branch of a Y-shaped drift tube sub-section $38_1$ having another ion outlet branch coupled to an ion inlet of another drift tube funnel $32_{11}$, wherein both such ion outlet branches are coupled to a common ion inlet branch having an ion inlet coupled to an ion outlet of the drift tube funnel $32_2$. The drift tube funnel $32_4$ is similarly coupled at its ion outlet to one ion inlet branch of another Y-shaped drift tube sub-section $38_2$ having another ion inlet branch coupled to an ion outlet of the drift tube funnel $32_{11}$, wherein both such ion outlet branches are coupled to a common ion outlet branch having an ion outlet coupled to an ion outlet of the drift tube funnel $32_9$. In this embodiment, the single-pass drift tube 12' is a linear drift tube made up of the linear drift tube segments D1 and D2 joined by a linear drift tube segment D3 made up of the linear branches of the Y-shaped drift tube sub-sections $38_1$, $38_2$ and the drift tube funnel $32_{11}$.

The embodiment illustrated in FIG. 1B includes four ion gates G1-G4 which are controllable, as will be described in detail below, to confine ions within the single-pass drift tube 12', to confine ions within the multiple-pass drift tube 14, to pass or divert at least some of the ions in the single-pass drift tube 12' into the multiple-pass drift tube 14 and/or to pass or divert at least some of the ions in the multiple-pass drift tube 14 back into the single-pass drift tube 12'. A first one of the ion gates, G1, is illustratively positioned in the Y-shaped drift tube section $38_1$ at an interface of the curved branch of the Y-shaped drift tube section $38_1$ that is coupled to the drift tube funnel $32_1$ and the branch of the Y-shaped drift tube section $38_1$ that is coupled to the drift tube funnel $32_2$. A second one of the ion gates, G2, is illustratively positioned in the Y-shaped drift tube section $38_1$ at an interface of the linear branch of the Y-shaped drift tube section $38_1$ that is coupled to the drift tube funnel $32_{11}$ and the branch of the Y-shaped drift tube section $38_1$ that is coupled to the drift tube funnel $32_2$. A third one of the ion gates, G3, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_8$. A fourth one of the ion gates, G4, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_4$. It will be understood that the hybrid ion mobility spectrometer 10' may include more or fewer such ion gates, and that any such alternative embodiment of the hybrid ion mobility spectrometer is contemplated by this disclosure.

Figure 1C:
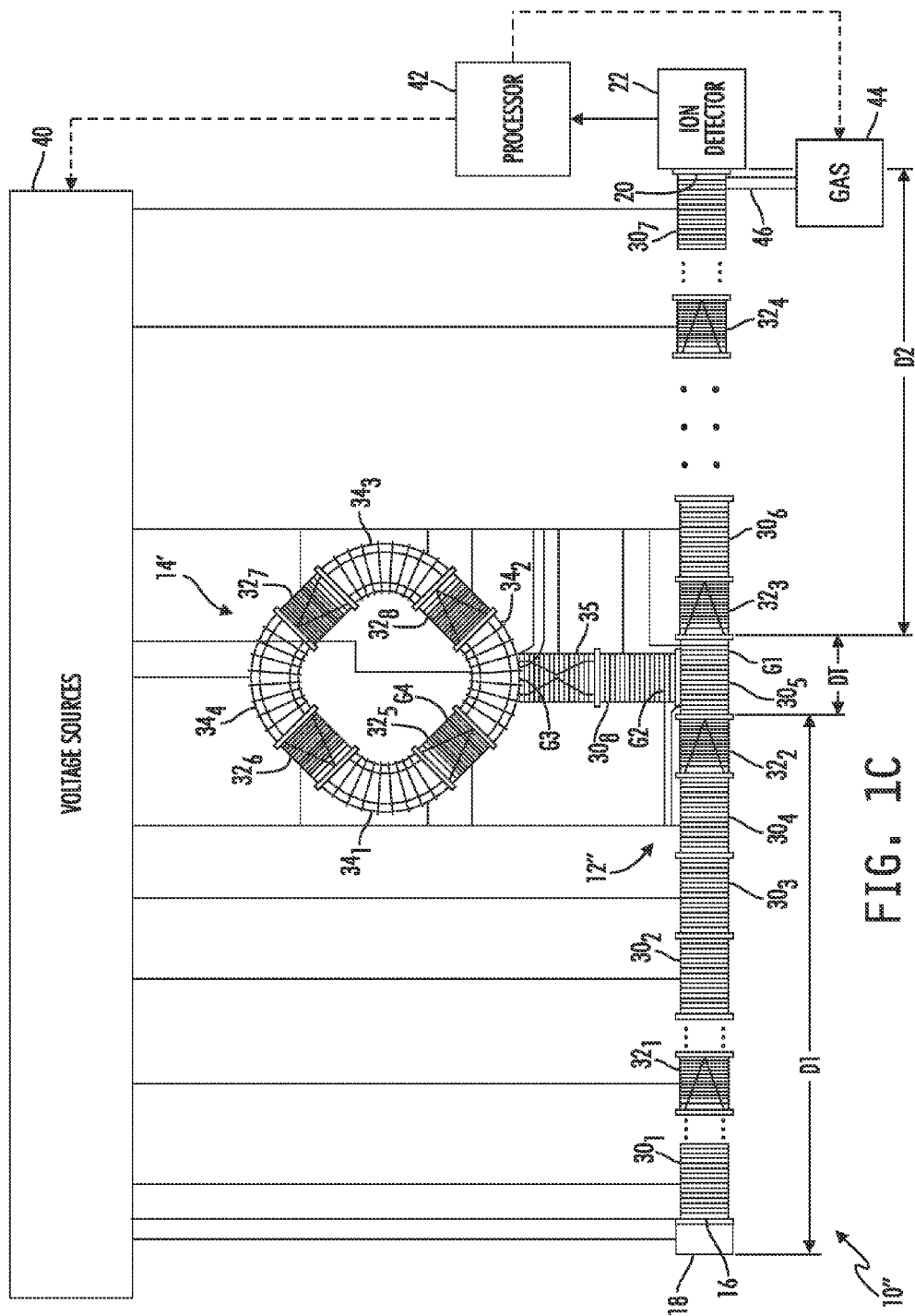
FIG. 1C is a simplified diagram of another alternate embodiment of a hybrid ion mobility spectrometer.

Referring now to FIG. 1C, another alternate embodiment of a hybrid ion mobility spectrometer 10" is shown. The hybrid ion mobility spectrometer 10" is also identical in many respects to the hybrid ion mobility spectrometer 10 illustrated in FIG. 1A and described above. Like features are identified by like reference numbers, and a detailed description of common features between the two spectrometers 10 and 10" will not be repeated here for brevity. It will be further understood that the various embodiments of the various components and aspects to the hybrid ion mobility spectrometer 10 described above apply equally to the hybrid ion mobility spectrometer 10".

The hybrid ion mobility spectrometer 10" illustrated in FIG. 1C differs from the hybrid ion mobility spectrometer 10 illustrated in FIG. 1A primarily in the construction of each of the single-pass drift tube 12" and the multiple-pass drift tube 14', and also in the location of the various ion gates that are controlled to achieve operation of the spectrometer 10 as described above. In the embodiment illustrated in FIG. 1C, for example, the drift tube funnel $32_2$ is coupled at its ion outlet to an ion inlet of a drift tube sub-section $30_5$, and an ion outlet of the drift tube sub-section $30_5$ is coupled to an ion inlet of the drift tube funnel $32_3$ (corresponding to the drift tube funnel $32_9$ in FIG. 1A). In this embodiment, the single-pass drift tube 12" is thus a linear drift tube made up of the linear drift tube segments D1 and D2 joined by a linear drift tube segment DT made up of the drift tube sub-section $30_5$. The multiple-pass drift tube 14' is, in the embodiment illustrated in FIG. 1C, a closed-path drift tube made up of four curved drift tube sub-sections $34_1$-$34_4$ each coupled between a different two of four drift tube funnels $32_5$-$32_8$. A drift tube section $30_8$ has an ion inlet coupled to the drift tube sub-section $30_5$ of the single-pass drift tube 12" and an ion outlet coupled to an ion inlet of a drift tube section 35. An ion outlet of the drift tube section 35 is coupled to the drift tube sub-section $34_2$ of the multiple pass drift tube 14'. In some embodiments, such as that illustrated in FIG. 1C, the drift tube section 35 may include an inlet/outlet, i.e. bi-directional, funnel which may be controlled in a conventional manner, e.g., via one or more voltage sources, to direct and focus ions moving from the single-pass drift tube 12" into the multiple-pass drift tube 14' via the drift tube sub-section 30$_8$, and which may also be controlled in a conventional manner, e.g., via one or more voltage sources, to direct and focus ions moving from the multiple-drift tube 14' into the single-pass drift tube 12" via the drift tube sub-section 30$_8$. In other embodiments, the bi-directional funnel may be replaced with another funnel structure or other mechanism (e.g., structure and/or energy source(s)), or omitted altogether. In any case, the drift tube sections 30$_8$, 35 form a T-connection between the single pass drift tube 12" and the multiple-pass drift tube 14'.

The embodiment illustrated in FIG. 1C includes three ion gates G1-G3 which are controllable, as will be described in detail below, to confine ions within the single-pass drift tube 12", to confine ions within the multiple-pass drift tube 14', to pass or divert at least some of the ions in the single-pass drift tube 12" into the multiple-pass drift tube 14' and/or to pass or divert at least some of the ions in the multiple-pass drift tube 14' back into the single-pass drift tube 12". A first one of the ion gates, G1, is illustratively positioned in the drift tube sub-section 30$_5$ at or just beyond the ion inlet of the drift tube section 30$_8$. A second one of the ion gates, G2, is illustratively positioned in the drift tube section 30$_8$ at or just beyond the ion inlet thereof. A third one of the ion gates, G3, is illustratively positioned in the drift tube section 35 at or near the ion outlet thereof. It will be understood that the hybrid ion mobility spectrometer 10" may include more or fewer such ion gates, and that any such alternative embodiment of the hybrid ion mobility spectrometer is contemplated by this disclosure.

Figure 1D:
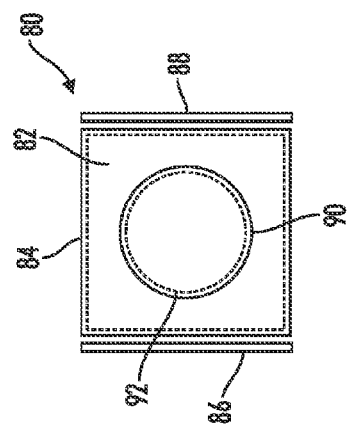
FIG. 1D is a simplified diagram of yet another alternate embodiment of a hybrid ion mobility spectrometer.
Figure 1F:
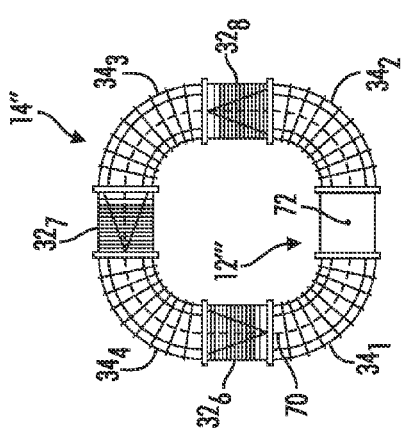
FIG. 1F is a simplified diagram of an embodiment of the transition region of the hybrid ion mobility spectrometer illustrated in FIGS. 1D and 1E.
Figure 1E:
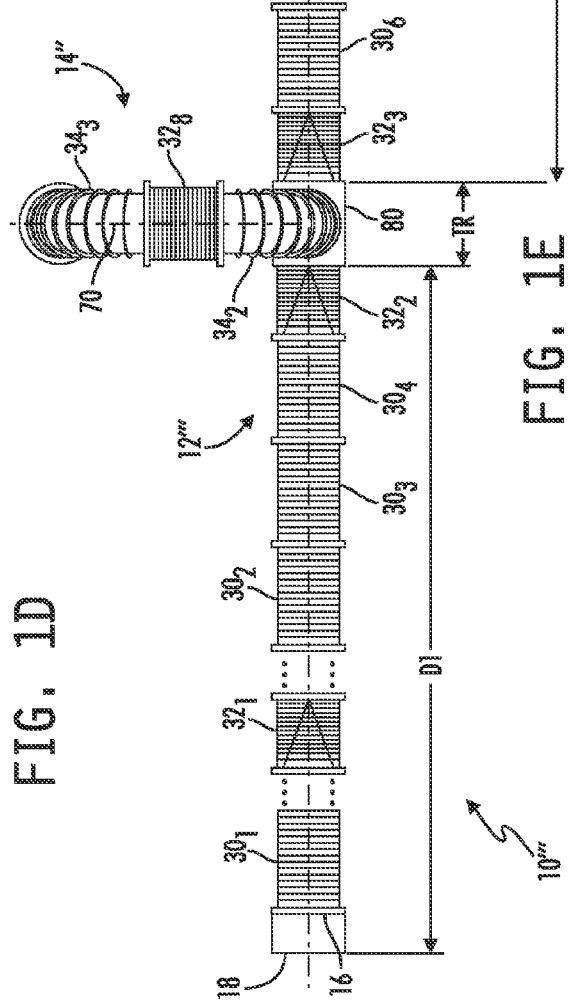
FIG. 1E is a simplified diagram of the embodiment illustrated in FIG. 1D viewed orthogonally from the view illustrated in FIG. 1D.

Referring now to FIGS. 1D-1F, yet another alternate embodiment of a hybrid ion mobility spectrometer 10''' is shown. The hybrid ion mobility spectrometer 10''' is also identical in many respects to the hybrid ion mobility spectrometers 10 and 10" illustrated in FIGS. 1A and 1C respectively and described above. Like features are identified by like reference numbers, and a detailed description of common features between the spectrometers 10, 10" and 10''' will not be repeated here for brevity. It will be further understood that the various embodiments of the various components and aspects to the hybrid ion mobility spectrometer 10 and 10" described above apply equally to the hybrid ion mobility spectrometer 10'''.

In one aspect, the hybrid ion mobility spectrometer 10''' illustrated in FIGS. 1D-1F differs from the hybrid ion mobility spectrometer 10 and 10" illustrated in FIGS. 1A and 1C respectively in that an ion travel axis 70 of the multiple-pass drift tube 14", i.e., an axis defined, or parallel with an axis defined, centrally through the multiple-pass drift tube 14" and along which ions travel through the multiple-pass drift tube 14", lies in a plane that is different from the plane in which an ion travel axis 72 of the single-pass drift tube 12''', i.e., an axis defined, or parallel with an axis defined, centrally through the single-pass drift tube 12''' and along which ions travel through the single-pass drift tube 12''', lies. In the illustrated embodiment, the planes in which the ion travel axes 70 and 72 lie are orthogonal, although it will be understood that this disclosure contemplates embodiments in which the two different planes in which the ion travel axes 70 and 72 lie are not orthogonal.

In another aspect, the hybrid ion mobility spectrometer 10''' illustrated in FIGS. 1D-1F differs from the hybrid ion mobility spectrometer 10 and 10" illustrated in FIGS. 1A and 1C respectively in that, in contrast to a drift tube transition section, DT, the hybrid ion mobility spectrometer 10''' defines a transition region 80 (TR) as an interface between the single-pass drift tube 12''' and the multiple-pass drift tube 14". Referring specifically to FIG. 1F, an example embodiment of the transition region 80 is illustrated. In this embodiment, the transition region 80 includes a first plate 82 defining an ion passage, e.g., opening, 90 therethrough, which represents an ion inlet to the transition region 80 positioned adjacent to the ion outlet of the drift tube funnel 32$_2$ (e.g., see FIG. 1E). Another plate 84 is positioned opposite to the plate 80 and defines another ion passage, e.g., opening, 92 therethrough (both shown by dashed-line representation in FIG. 1F), which represents an ion outlet of the transition region 80 positioned adjacent to the ion inlet of the drift tube funnel 32$_3$. A third plate 86 is positioned between the plates 82 and 84 along one side thereof, and a fourth plate 88 is positioned between the plates 82 and 84 along another side thereof. The third and fourth plates 86, 88 each define an ion passage, e.g., opening, therethrough which represent an ion inlet/outlet to/of the transition region 80 with the opening defined through the plate 86 positioned adjacent to the ion inlet/outlet of the drift tube sub-section 34$_1$ and the opening defined through the plate 88 positioned adjacent to the ion inlet/outlet of the drift tube section 34$_2$. One or more of the plates 82, 84, 86, 88 may illustratively be operated as an ion gate, such that the illustrated embodiment may include one or more of G1-G4.

Figure 3A:
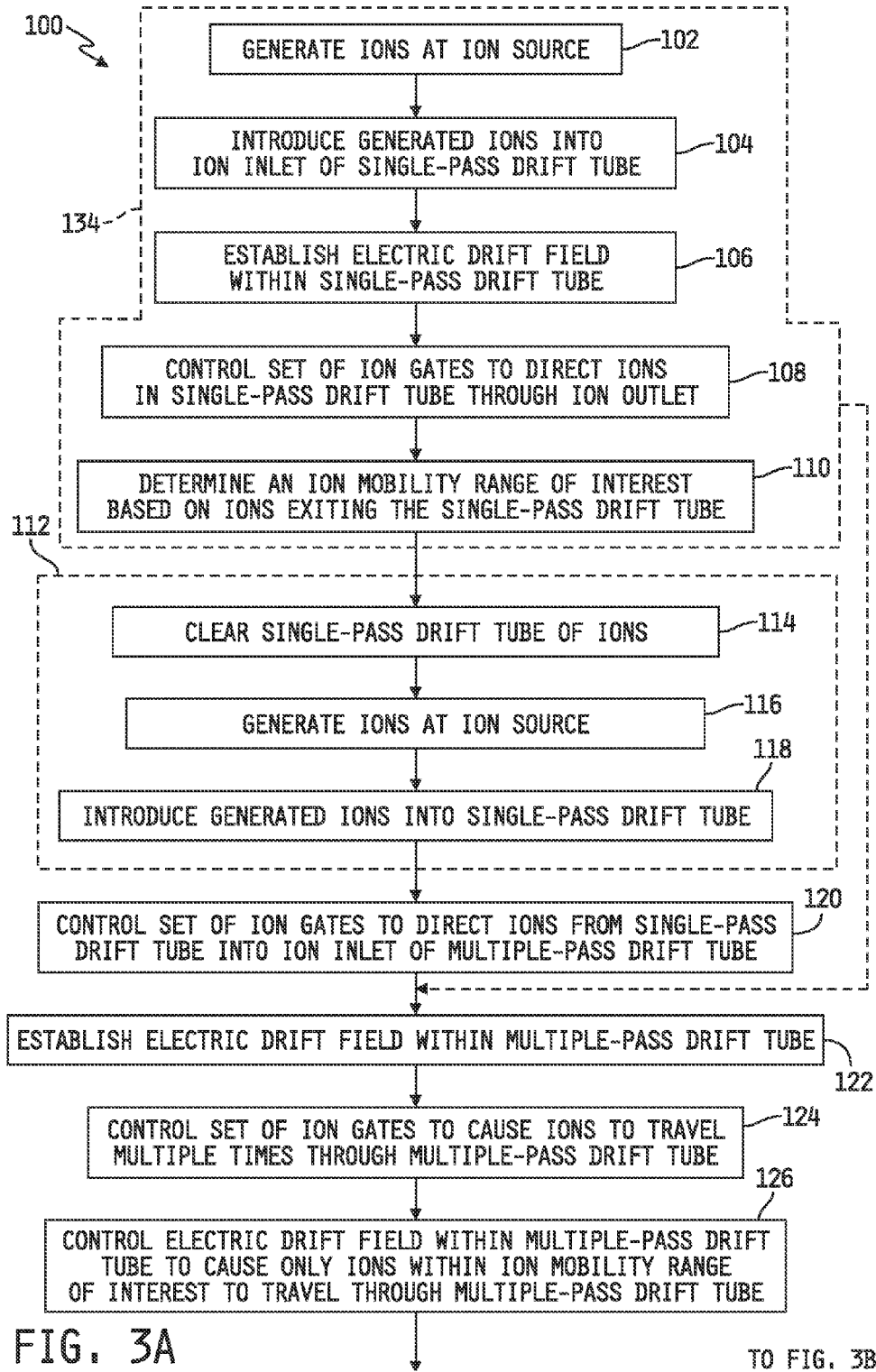
FIG. 3 includes FIGS. 3A and 3B and is a simplified flowchart of an embodiment of a process for separating ions using any of the hybrid ion mobility spectrometers of FIGS. 1A-1F.
Figure 3B:
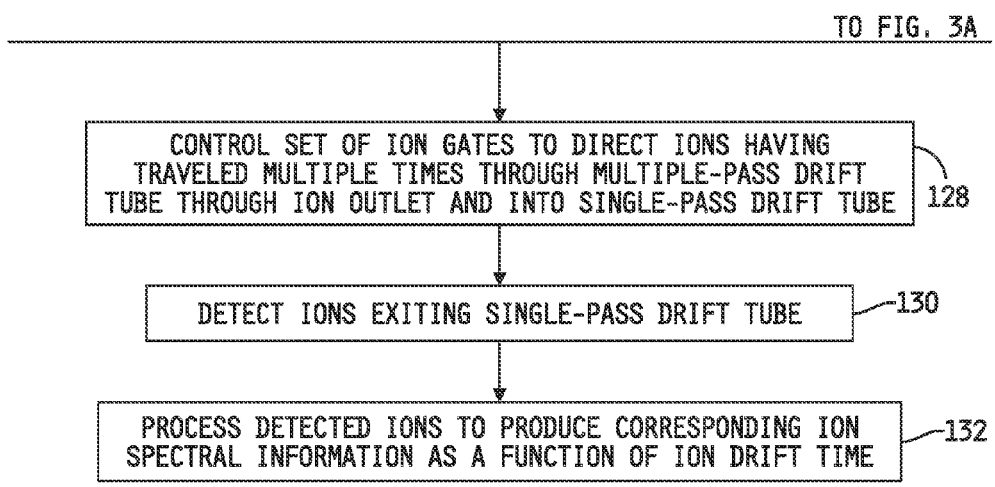

As described briefly hereinabove, the ion gates G1-G3 of the hybrid ion mobility spectrometers 10 and 10" and the ion gates G1-G4 of the hybrid ion mobility spectrometer 10' and 10''' are controllable to confine ions within the single-pass drift tube 12, 12', 12", 12''', to confine ions within the multiple-pass drift tube 14, 14', 14" to pass or divert at least some of the ions in the single-pass drift tube 12, 12', 12", 12''' into the multiple-pass drift tube 14, 14', 14" and/or to pass or divert at least some of the ions in the multiple-pass drift tube 14, 14', 14" back into the single-pass drift tube 12, 12', 12", 12'''. Referring now to FIGS. 3A and 3B, a flowchart is shown illustrating a process 100 for controlling the hybrid ion mobility spectrometer 10, 10', 10", 10''' according to a number of different operational modes of the hybrid ion mobility spectrometer 10, 10', 10", 10''' in which the set of ion gates, e.g., ion gates G1-G3 for the spectrometers 10, 10" and ion gates G1-G4 for the spectrometer 10', 10''', are controlled as described above. In one embodiment, some or all of the process 100 may be controlled by the processor 42 in accordance with instructions stored in a memory of the processor 42. Alternatively or additionally, some or all of the process 100 may be controlled by programming one or more of the one or more voltage sources 40 in embodiments in which one or more of the voltage sources 40 are programmable. Some of the process 100 may be alternatively or additionally carried out manually.

In any case, the process 100 begins at step 102 where the ion source 18 is controlled in a conventional manner to generate ions, e.g., in embodiments in which the ion source 18 is or includes an ion generation structure for generating ions from a sample, or to otherwise supply ions, e.g., in embodiments in which the ion source 18 is another ion separation instrument and/or other ion processing instrument that does not itself generate ions but rather operates on ions generated elsewhere. Thereafter at step 104, at least some of the generated or otherwise supplied ions are introduced into the ion inlet 16 of the single-pass drift tube 12, 12', 12", 12''', e.g., by controlling a conventional ion gate positioned at the ion inlet 16 to pass ions therethrough and into the single-pass drift tube 12, 12', 12", 12'", by drawing generated ions into the single-pass drift tube 12, 12', 12", 12'" using a static or dynamic electric field, or the like. At step 106, an electric drift field is established within the single-pass drift tube 12, 12', 12", 12'", which may occur before or after step 104.

In any case, the process 100 advances to step 108 where the ion gates, e.g., G1-G3 in the case of the hybrid ion mobility spectrometer 10, 10" and G1-G4 in the case of the hybrid ion mobility spectrometer 10', 10'", are controlled to direct ions in the single-pass drift tube 12, 12', 12", 12'" therethrough and through the ion outlet 20, i.e., to confine ions within the single-pass drift tube 12, 12', 12", 12'" such that the ions drift only through the single-pass drift tube 12, 12', 12", 12'" from the ion inlet 16 to the ion outlet 20 thereof and not through the multiple-pass drift tube 14, 14', 14". In the single-pass drift tube 12 illustrated in FIG. 1A, step 108 may be carried out by controlling G1 to the closed or ion-blocking position and controlling G2 and G3 to the open or ion-passing position, such that ions entering the ion inlet 16 pass sequentially through D1, DT and D2 of the single-pass drift tube 12. In the single-pass drift tube 12' illustrated in FIG. 1B, step 108 may be carried out by controlling G1 to the closed or ion-blocking position and controlling G2 to the open or ion-passing position, such that ions entering the ion inlet 16 pass sequentially through D1, D3 and D2 of the single-pass drift tube 12'. In the single-pass drift tube 12" illustrated in FIG. 1C, step 108 may be carried out by controlling G1 to the open or ion-passing position and controlling G2 to the closed or ion-blocking position, such that ions entering the ion inlet 16 pass sequentially through D1, DT and D2 of the single-pass drift tube 12". In the single-pass drift tube 12'" illustrated in FIGS. 1D-1F, step 108 may be carried out by controlling G1, e.g., the opening 90 through the plate 82, to the open or ion-passing position and controlling G2, e.g., the opening 92 through the plate 84, to the open or ion-passing position, and likewise controlling the gates G3, G4, e.g., the openings through the plates 86, 88 respectively to the closed or ion blocking positions, such that ions entering the ion inlet 16 pass sequentially through D1, TR and D2 of the single-pass drift tube 12'". In each case, ions generated at or otherwise supplied by the ion source 18 travel, i.e., drift, through only the single-pass drift tube 12, 12', 12", 12'" under the influence of the electric field established therein where they separate in time as a first function of ion mobility defined by the various structural dimensions and operating parameters of the single-pass drift tube 12, 12', 12", 12'".

Following step 108, the process 100 advances to step 110 where an ion mobility range of interest is determined based on at least some of the ions exiting the single-pass drift tube 12, 12', 12", 12'". As described above, it may be discovered upon analysis of ion spectral information resulting from the detection of ions exiting the ion outlet 20 of the single-pass drift tube 12, 12', 12', 12"" pursuant to step 108 that a subset, e.g., two or more, of ion intensity peaks in a particular range of ion mobilities (or ion drift times) are crowded together and cannot be satisfactorily resolved over the length of the single-pass drift tube 12, 12', 12", 12'". Such a range of ion mobilities may then be the ion mobility range of interest. In other cases, the ion mobility range of interest may be determined based on one or more alternate or additional criteria. In some cases, the ion mobility range of interest may be the same as that produced by the single-pass drift tube 12, 12', 12", 12'", and in other cases the ion mobility range of interest may be different as just described. Likewise, whereas the single-pass drift tube 12, 12', 12", 12'" is generally operable to separate ions according to a first function of ion mobility and the multiple-pass drift tube 14, 14', 14" is generally operable to separate ions according to a second function of ion mobility, the first and second functions of ion mobility may be the same in some embodiments and different in others.

In one embodiment, the process 100 includes a step 112 as shown in dashed-line representation, and in this embodiment the process 100 advances from step 110 to step 114 wherein the single-pass drift tube 12, 12', 12", 12'" is cleared of ions, e.g., by stopping the generation of ions by the ion source 18 and allowing the tube 12, 12', 12", 12'" to clear. Thereafter at step 116, the ion source 18 is controlled to begin generating ions again, and thereafter at step 118 at least some of the generated ions are introduced into the single-pass drift tube 12, 12', 12", 12'" as described above with respect to step 104. In alternate embodiments, the process 100 does not include step 112 and in some such embodiments the ion source 18 may be controlled to continually, periodically or intermittently generate ions while in other embodiments the ion source 18 may be started and then stopped, but ions need not be cleared from the single-pass drift tube 12, 12', 12", 12'" before continuing to step 120.

At step 120, the set of ion gates, e.g., G1-G3 in the case of the hybrid ion mobility spectrometer 10, 10'" and G1-G4 in the case of the hybrid ion mobility spectrometer 10', 10'", is controlled to divert or pass some or all of the ions in or entering the single-pass drift tube 12, 12', 12", 12'" into the multiple-pass drift tube 14, 14', 14", and at step 122 an electric field is established within the multiple-pass drift tube 14, 14', 14" to cause ions to drift through the multiple-pass drift tube 14, 14', 14". In the single-pass drift tube 12 illustrated in FIG. 1A, step 120 may be carried out by controlling G1 and G3 to their open or ion-passing positions and controlling G2 to the closed or ion-blocking position, such that ions entering the ion inlet 16 pass sequentially through D1, through part of DT and into the multiple-pass drift tube 14. In the single-pass drift tube 12' illustrated in FIG. 1B, step 120 may be carried out by controlling G1 and G3 to their open or ion-passing positions, and controlling G2 and G4 to their closed or ion-blocking positions, such that ions entering the ion inlet 16 pass from D1 directly into the multiple-pass drift tube 14. In the single-pass drift tube 12" illustrated in FIG. 1C, step 120 may be carried out by controlling G1 to the closed or ion-blocking position, and controlling G2 and G3 to their open or ion-passing positions with the electric drift field in the drift tube sections $30_8$ and 35 controlled to pass ions moving through D1 into the multiple-pass drift tube 14'. In the single-pass drift tube 12'" illustrated in FIGS. 1D-1F, step 120 may be carried out by controlling G1, e.g., the opening 90 through the plate 82, to the open or ion-passing position, controlling G2, e.g., the opening 92 through the plate 84, to the closed or ion-blocking position, and controlling the gates G3 and/or G4, e.g., the openings through the plates 86, 88 respectively to the open or ion-passing positions, such that ions entering the ion inlet 16 pass from D1 through TR and directly into the multiple-pass drift tube 14". Ions generated at the ion source 18 thus travel, i.e., drift, through the single-pass drift tube 12, 12', 12", 12'" under the influence of the electric field established therein where they separate in time as a first function of ion mobility defined by the various structural dimensions and operating parameters of the single-pass drift tube 12, 12', 12", 12'", and after passage of some or all of such ions into the multiple-pass drift tube 14, 14', 14" the ions travel, i.e., drift, through the multiple-pass drift tube 14, 14', 14" under the influence of the electric field established therein where they separate in time as a second function of ion mobility defined by the various structural dimensions and operating parameters of the multiple-pass drift tube 14, 14', 14". The first and second functions of ion mobility may be the same in some embodiments and different in others.

At step 124, the set of ion gates, e.g., G1-G3 in the case of the hybrid ion mobility spectrometer 10, 10" and G1-G4 in the case of the hybrid ion mobility spectrometer 10', 10''', is controlled to cause ions within the multiple-pass drift tube 14, 14', 14" to travel one or multiple times through or about the multiple-pass drift tube 14, 14', 14". The number of times the ions travel through or about the multiple-pass drift tube 14, 14', 14" will typically be dictated by the total length of the multiple-pass drift tube 14, 14', 14" needed to adequately resolve the ion peaks of interest, or by other additional or alternate criteria. In the single-pass drift tube 12 illustrated in FIG. 1A, step 124 may be carried out by maintaining G1 in its open or ion-passing position and G2 in its closed or ion-blocking position, and controlling G3 to its closed position such that the multiple-pass drift tube 14 is completely closed to the single-pass drift tube 12. In the single-pass drift tube 12' illustrated in FIG. 1B, step 124 may be carried out by maintaining G3 and in its open or ion-passing position and G4 in its closed or ion-blocking position, and controlling G1 to its closed or ion-blocking position such that the multiple-pass drift tube 14 is completely closed to the single-pass drift tube 12'. In the single-pass drift tube 12" illustrated in FIG. 1C, step 124 may be carried out by controlling G2 and/or G3 to closed or ion-blocking position, such that the multiple-pass drift tube 14' is completely closed to the single-pass drift tube 12". In the single-pass drift tube 12''' illustrated in FIGS. 1D-1F, step 124 may be carried out by controlling G1, G2, e.g., the openings through the plates 82, 84 respectively, to their closed or ion-blocking positions, and controlling G3, G4, e.g., the openings through the plates 86, 88 respectively, to their open or ion-passing positions, such that the multiple-pass drift tube 14" is completely closed to the single-pass drift tube 12'''. The ions then travel, i.e., drift, through the multiple-pass drift tube 14, 14', 14" under the influence of the electric field established therein where they separate in time as a second function of ion mobility defined by the various structural dimensions and operating parameters of the multiple-pass drift tube 14, 14', 14".

In one embodiment, step 126 is included, and at step 126 the electric drift field established within the multiple-pass drift tube 14, 14', 14" is controlled to cause only ions within the ion mobility range of interest to travel through the multiple-pass drift tube 14, 14', 14". For example, the open/closed timing of the various ion gates (G1-G3 or G1-G4) may be controlled at step 120 to pass ions of all mobilities from the single-pass drift tube 12, 12', 12", 12''' into the multiple-pass drift tube 14, 14', 14", and in such embodiments, electric fields within the sub-sections 34 and funnels 32 of the multiple-pass drift tube 14, 14', 14" are sequentially switched on and off in a conventional manner at a rate that allows only ions within the ion mobility range of interest to traverse the multiple-pass drift tube 14, 14', 14". In some alternate embodiments, the open/closed timing of the ion gates G1-G3 (or G1-G4) may be controlled at step 120 such that only ions within the ion mobility range of interest are passed from the single-pass drift tube 12, 12', 12", 12''' into the multiple-pass drift tube 14, 14', 14", and in such embodiments step 126 may be carried out simply by controlling the application of the electric fields within the sub-sections 34 and funnels 32 of the multiple-pass drift tube 14, 14', 14" to pass ions of all ion mobilities or by sequentially switching such electric fields on and off at a rate that allows only ions within the ion mobility range of interest to continue to traverse the multiple-pass drift tube 14, 14', 14".

After the ions have traveled the multiple times through the multiple-pass drift tube 14, 14', 14" the set of ion gates, e.g., G1-G3 in the case of the hybrid ion mobility spectrometer 10, 10" and G1-G4 in the case of the hybrid ion mobility spectrometer 10', 10''' is controlled at step 128 to pass at least some of the ions from the multiple-pass drift tube 14, 14', 14" back into the single-pass drift tube 12, 12', 12", 12'''. In the single-pass drift tube 12 illustrated in FIG. 1A, step 128 may be carried out by controlling G1 to the closed or ion-blocking position and controlling G2 to the open or ion-passing position, such that ions traveling through the multiple-pass drift tube 14 pass back into the single-pass drift tube 12, i.e., sequentially via the Y-shaped drift tube segment $36_2$, the drift tube funnel $32_4$ and the curved drift tube sub-section $34_2$. In the single-pass drift tube 12' illustrated in FIG. 1B, step 128 may be carried out by controlling G3 to the closed or ion-blocking position and controlling G4 to the open or ion-passing position, such that ions traveling through the multiple-pass drift tube 14 pass back into the single-pass drift tube 12', i.e., sequentially via the Y-shaped drift tube segment $36_2$, the drift tube funnel $32_4$ and the curved branch of the Y-shaped drift tube sub-section $38_2$. In the single-pass drift tube 12" illustrated in FIG. 1C, step 128 may be carried out by controlling G1, G2 and G3 to their open or ion-passing positions with the electric fields in the drift tube sections $30_8$ and 35 set to direct ions from the drift tube $34_2$ to the drift tube sub-section $30_5$. In the single-pass drift tube 12''' illustrated in FIGS. 1D-1F, step 128 may be carried out by controlling G1 and either G3 or G4, e.g., the openings through the plates 82 and 86 or 88 respectively, to their closed or ion-blocking positions, and controlling G2 and the other of G3 or G4, e.g., the openings through the plates 84 and 88 or 86 respectively, to their open or ion-passing positions, such that ions traveling through the multiple-pass drift tube 14" pass back into the single-pass drift tube 12''' via the transition region 80.

In one embodiment, ions re-entering the single-pass drift tube 12, 12', 12", 12''' travel, i.e., drift, through the remainder of the single-pass drift tube 12, 12', 12" toward and through the ion outlet 20 under the influence of the electric field established therein where they separate in time in D2 according to the first function of ion mobility. In some alternate embodiments, the open/closed timing of the ion gates G1-G3 (or G1-G4) may be controlled at step 120 such that ions within all ion mobility ranges are passed from the single-pass drift tube 12, 12', 12", 12''' into the multiple-pass drift tube 14, 14', 14", step 126 may be replaced by a step in which the open/closed timing of the ions gates G1-G3 (or G1-G4) are likewise controlled such that ions within all ion mobility ranges travel through the multiple-pass drift tube 14, 14', 14", step 128 may be modified to control the open/closed timing of the ion gates G1-G3 (or G1-G4) such that ions within all ion mobility ranges are passed from the multiple-pass drift tube 14, 14', 14" back into the single-pass drift tube 12, 12', 12", 12''', and one or more additional ion gates within D2, e.g., an ion gate positioned at the ion outlet 20, may be controlled by selectively controlling the open/closed positions of the one or more additional ion gates, e.g., relative to an opening/closing of one or more upstream ion gates, such that only ions within the ion mobility range of interest exit the ion outlet 20 of the single-pass drift tube 12, 12', 12", 12'''.

Ions traveling through the ion outlet 20 are detected at step 130 by the ion detector, and thereafter at step 132 the detected ions are processed by the processor 42 to produce corresponding ion spectral information, e.g., as a function of ion drift time.

In an alternate embodiment, the process 100 illustratively includes a step 134 between steps 120 and 122 such that the single-pass drift tube 12, 12', 12", 12''' and the multiple-pass drift tube 14, 14', 14" operate in parallel as described hereinabove. In one embodiment, step 134 may include steps 102-110 as illustrated in FIG. 3A. In other embodiments, step 134 may include only steps 102-108, and in still other embodiments in which ions are generated or otherwise supplied continually, intermittently or periodically step 134 may include only steps 104-108 or 104-110. In other embodiments still, step 134 may include more, fewer and/or other steps than those just described. In any such embodiments, one or more of the ion gates in the set of ion gates, e.g., G1-G3, may be controlled to one or more intermediate positions between the open and closed positions to direct some of the ions traveling through the single-pass drift 12 into the multiple-pass drift tube 14 while also allowing others of the ions traveling through the single-pass drift tube 12 to travel completely through the single-pass drift tube 12, e.g., to and through the outlet 20 thereof. In such a parallel operating mode, ions supplied by the single or common ion source 18 to the inlet 16 of the single-pass drift tube 12 thus travel in parallel through the single-pass drift tube 12 and also through the combination of the single-pass drift tube 12 and the multiple-pass drift tube 14, with some of the ions traveling directly through the single-pass drift tube 12 to and through the ion outlet 20 and others of the ions traveling through the single-pass drift tube 12, to and through the multiple-pass drift tube 14, then back to and through any remaining section(s) of the single-pass drift tube 12 and exiting the ion outlet 20 of the single-pass drift tube 12.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, in some alternate embodiments, one or more conventional ion analytical instruments may be substituted for either or both of the ion source 18 and the ion detector 22 such that alternate and/or additional ion separation, ion conformation alteration, ion processing and/or ion analysis may be carried out on ions prior to entering and/or after exiting the single-pass drift tube 12, 12', 12", 12'''. Alternatively or additionally, one or more conventional ion analytical instruments may be positioned within or interposed along either or both of the single-pass drift tube 12, 12', 12", 12''' and the multiple-pass drift tube 14, 14', 14" such that alternate and/or additional ion separation, ion conformation alteration, ion processing and/or ion analysis may be carried out within or along the single-pass drift tube 12, 12', 12", 12''' and/or the multiple-pass drift tube 14, 14', 14". In any case, examples of such conventional ion analytical instruments that precede the ion inlet 16 of the single-pass drift tube 12, 12', 12", 12''', that follow the ion outlet 20 of the single-pass drift tube 12, 12', 12", 12''' and/or that are positioned within or interposed along the single-pass drift tube 12, 12', 12", 12''' and/or the multiple-pass drift tube 14, 14', 14" may include, but are not limited to, one or more drift tubes identical to or different from the single-pass drift tube 12, 12', 12", 12''' and/or the multiple-pass drift tube 14, 14', 14", one or more mass analyzers and/or mass spectrometers, one or more liquid and/or gas chromatographs, one or mass filters (e.g., one or more multiple-pole mass filters), one or more collision cells and/or other ion fragmentation devices or regions, one or more ion activation regions in which an electric field is established that is high enough to alter the conformation of one or more ions but not high enough to fragment ions, or the like. It will be further understood that in embodiments that include two or more such conventional ion analytical instruments together, such two or more conventional ion analytical instruments may be positioned in parallel relative to each other, in series relative to each other (i.e., cascaded) or any combination of series and parallel.

Additionally or alternatively, those skilled in the art will recognize that the multiple-pass drift tube 14 illustrated in any of FIGS. 1A-1B can, in some embodiments, be provided in the form of two or more series-connected and/or parallel-connected multiple-pass drift tubes. Alternatively or additionally still, such one or more multiple-pass drift tubes 14 can be augmented by one or more single-pass drift tubes 12 and/or by one or more conventional analytical instruments of the type described by example in the previous paragraph.

As another example, it will be understood that while the various embodiments of the hybrid ion mobility spectrometer 10, 10', 10", 10''' illustrated and described herein include a multiple-pass drift tube 14, 14', 14" coupled to a single-pass drift tube 12, 12', 12", 12''' between an ion inlet 16 and an ion outlet 20 of the single-pass drift tube 12, 12', 12", 12''', this disclosure contemplates alternative embodiments in which the multiple-pass drift tube 14, 14', 14" or other suitable multiple-pass drift tube is positioned upstream of the single-pass drift tube 12, 12', 12", 12''', i.e., prior to the ion inlet 16 and/or downstream of the single-pass drift tube 12, 12', 12", 12''', i.e., following the ion outlet 20.

As still another example, operation of the ion gates G1-G3 or G1-G4 has been described herein in which such ion gates G1-G3 or G1-G4 are controlled to block or allow passage therethrough of some or all ions from a preceding, e.g. upstream, stage or section of the hybrid ion mobility spectrometer 10, 10', 10", 10'''. It will be understood that this disclosure contemplates embodiments in which any one or more of the gates G1-G3 or G1-G4 may be controlled to intermediate positions, i.e., between their open and closed positions, to allow pass therethrough of only a fraction of the ions at any one or more times. This would allow, for example, operation of the single-pass drift tube 12, 12', 12", 12''' to be carried out simultaneously with the operation of the multiple-pass drift tube 14, 14', 14" such that ions exiting more quickly from the single-pass drift tube 12, 12', 12", 12''' can be analyzed prior to analyzing ions exiting the multiple-pass drift tube.

What is claimed is:

1. A hybrid ion mobility spectrometer comprising:
a single-pass drift tube having an ion inlet at one end and an ion outlet at an opposite end, the single-pass drift tube configured to separate in time ions entering the ion inlet thereof and traveling therethrough according to a first function of ion mobility,
a multiple-pass drift tube having an ion inlet and an ion outlet each coupled to the single pass drift tube between the ion inlet of the single-pass drift tube and the ion outlet of the single-pass drift tube, the multiple-pass drift tube configured to separate in time ions entering the ion inlet of the multiple-pass drift tube and traveling one or more times therethrough according to the first or a second function of ion mobility, and a set of ion gates each controllable between an open position to pass ions therethrough and a closed position to block ions from passing therethrough, the set of ion gates controlled between the open and closed positions to selectively pass at least some of the ions traveling through the single-pass drift tube into the multiple-pass drift tube via the ion inlet of the multiple-pass drift tube and to selectively pass at least some of the ions traveling through the multiple-pass drift tube into the single-pass drift tube via the ion outlet of the multiple-pass drift tube.

2. The hybrid ion mobility spectrometer of claim 1 wherein each of the set of ions gates is controllable to the open position in response to a different first ion gate control signal and is controllable to the closed position in response to a different second ion gate control signal, and further comprising a first plurality of voltage sources to produce the different first and second ion gate control signals.

3. The hybrid ion mobility spectrometer of claim 2 wherein one or more voltage sources within the first plurality of voltage sources is programmable to control timing of production of at least one of the different first ion gate control signals and at least one of the different second ion gate control signals.

4. The hybrid ion mobility spectrometer of claim 2 further comprising a processor electrically coupled to at least one of the first plurality of voltage sources, the processor to control timing of production of at least one of the different first ion gate control signals and at least one of the different second ion gate control signals.

5. The hybrid ion mobility spectrometer of claim 2 wherein the single-pass drift tube is responsive to a first set of voltage signals to separate ions in time according to the first function of ion mobility and the multiple-pass drift tube is responsive to a second set of voltage signals to separate ions in time according to the first or second function of ion mobility, and further comprising a second plurality of voltage sources to produce the first and second sets of voltage signals.

6. The hybrid ion mobility spectrometer of claim 1 wherein the set of ions gates define:

a first combination of open and closed positions of the set of ion gates that directs ions to travel through the single-pass drift tube while blocking ions from entering the ion inlet of the multiple-pass drift tube, such that ions entering the ion inlet of the single-pass drift tube travel completely through the single-pass drift tube and exit the ion outlet thereof, a second combination of open and closed positions of the set of ion gates that directs at least some of the ions traveling through the single-pass drift tube into the ion inlet of the multiple-pass drift tube, a third combination of open and closed positions of the set of ion gates that directs ions in the multiple-pass drift tube to travel multiple times therethrough while blocking ions traveling through the multiple-pass drift tube from exiting the ion outlet thereof and re-entering the single-pass drift tube, and a fourth combination of open and closed positions of the set of ion gates that directs at least some of the ions traveling through the multiple-pass drift tube through the ion outlet thereof and into the single-pass drift tube, wherein ions entering the single-pass drift tube from the ion outlet of the multiple-pass drift tube travel toward and exit through the ion outlet of the single-pass drift tube.

7. The hybrid ion mobility spectrometer of claim 1 wherein the multiple-pass drift tube comprises a closed-path drift tube, the ion inlet of the multiple-pass drift tube comprises an ion inlet tube having an ion outlet integrally formed with the multiple-pass drift tube and the ion outlet of the multiple-pass drift tube comprises an ion outlet tube having an ion inlet integrally formed with the multiple-pass drift tube.

8. The hybrid ion mobility spectrometer of claim 7 wherein the single-pass drift tube comprises a first plurality of cascaded drift tube segments, wherein the closed-path drift tube comprises a second plurality of cascaded drift tube segments with an ion outlet of a last one of the second plurality of cascaded drift tube segments coupled to an ion inlet of a first one of the second plurality of cascaded drift tube segments, and wherein at least one of the first plurality of drift tube segments and at least one of the second plurality of drift tube segments define at least one common drift tube segment.

9. The hybrid ion mobility spectrometer of claim 7 wherein the single-pass drift tube comprises a first plurality of linearly arranged, cascaded drift tube segments, wherein the closed-path drift tube comprises a second plurality of cascaded drift tube segments with an ion outlet of a last one of the second plurality of cascaded drift tube segments coupled to an ion inlet of a first one of the second plurality of cascaded drift tube segments, and wherein the ion inlet of the multiple-pass drift tube is coupled to one of the first plurality of drift tube segments and the ion outlet of the multiple-pass drift tube is coupled to another of the first plurality of drift tube segments downstream of the one of the first plurality of drift tube segments.

10. The hybrid ion mobility spectrometer of claim 1 wherein the single-pass drift tube comprises a first plurality of linearly arranged, cascaded drift tube segments, wherein the multiple-pass drift tube comprises a closed-path drift tube, the closed-path drift tube comprising a second plurality of cascaded drift tube segments with an ion outlet of a last one of the second plurality of cascaded drift tube segments coupled to an ion inlet of a first one of the second plurality of cascaded drift tube segments, and wherein the ion inlet and the ion outlet of the multiple-pass drift tube together comprise an ion inlet-outlet tube coupled at one end to one of the first plurality of drift tube segments between the ion inlet of the single-pass drift tube and the ion outlet of the single-pass drift tube and at an opposite end to one of the second plurality of drift tube segments.

11. The hybrid ion mobility spectrometer of claim 1 further comprising an ion source coupled to the ion inlet of the single-pass drift tube, the ion source configured to generate ions from a sample.

12. The hybrid ion mobility spectrometer of claim 1 further comprising an ion detector to detect ions exiting the ion outlet of the single-pass drift tube and to produce an ion detection signal corresponding thereto.

13. The hybrid ion mobility spectrometer of claim 12 further comprising a processor to process the ion detection signal and produce corresponding ion mobility spectral information as a function of ion drift time.

14. The hybrid ion mobility spectrometer of claim 1 wherein each of the set of ion gates is controllable to at least one intermediate position to pass at least some ions therethrough, one or more of the set of ion gates controlled to the at least one intermediate position to selectively pass some of the ions traveling through the single-pass drift tube into the multiple-pass drift tube while also allowing others of the ions traveling through the single-pass drift to travel through the single-pass drift tube to the outlet thereof.

15. A method for separating ions comprising:
   introducing ions into an ion inlet of a first drift tube,
      establishing at least a first electric field within the first drift tube to cause at least some of the ions introduced into the ion inlet thereof to travel through the first drift tube from the ion inlet thereof toward an ion outlet thereof while separating in time according to a first function of ion mobility,
      controlling a set of ion gates to direct at least some of the ions traveling through the first drift tube into a second drift tube via an ion inlet of the second drift tube that is coupled to the first drift tube between the ion inlet of the first drift tube and the ion outlet of the first drift tube,
      establishing at least a second electric field within the second drift tube to cause ions entering the ion inlet thereof to travel through the second drift tube while separating in time according to the first or a second function of ion mobility, controlling the set of ion gates to cause ions traveling through the second drift tube to travel through the second drift tube multiple times, and
      controlling the set of ion gates to direct at least some of the ions having traveled the multiple times through the second drift tube into the first drift tube via an ion outlet of the second drift tube that is coupled to the first drift tube between the ion inlet of the first drift tube and the ion outlet of the first drift tube,
      wherein at least some of the ions passing into the first drift tube from the ion outlet of the second drift tube travel toward and exit through the ion outlet of the first drift tube.

16. The method of claim 15 wherein introducing ions into the ion inlet of the first drift tube comprises introducing a first set of ions into the ion inlet of the first drift tube, and further comprising:
   controlling the set of ion gates to cause the first set of ions to travel through the first drift tube and exit through the ion outlet of the first drift tube,
   determining, based on the first set of ions exiting the ion outlet of the first drift tube, a range of ion mobilities of at least some of the first set of ions, and
   introducing a second set of ions into the ion inlet of the first drift tube after introducing the first set of ions into the ion inlet of the first drift tube,
   wherein controlling the set of ion gates to direct at least some of the ions traveling through the first drift tube into the second drift tube comprises controlling the set of ion gates to direct the second set of ions traveling through first drift tube into the second drift tube via the ion inlet of the second drift tube,
   and further comprising controlling the second electric field to cause only ions in the second set of ions that are within the determined range of ion mobilities to travel through the second drift tube,
   wherein controlling the set of ion gates to direct at least some of the ions having traveled the multiple times through the second drift tube into the first drift tube comprises controlling the set of ion gates to direct ions from the second set of ions that are traveling through the second drift tube into the first drift tube via the ion outlet of the second drift tube,
   and wherein the ions from the second set of ions passing into the first drift tube from the ion outlet of the second drift tube exit through the ion outlet of the first drift tube and have ion mobilities only within the defined range of ion mobilities.

17. The method of claim 16 further comprising generating the first and second sets of ions from a common sample.

18. The method of claim 15 wherein the second drift tube defines a closed path, the ion inlet of the second drift tube comprises an ion inlet tube integrally formed with the second drift tube and the ion outlet of the second drift tube comprises an ion outlet tube also integrally formed with the second drift tube,
   and wherein controlling the set of ion gates to cause ions traveling through the second drift tube to travel through the second drift tube multiple times comprises controlling the set of ion gates to block the ions traveling through the second drift tube from exiting the second drift tube via the ion outlet of the second drift tube and to direct the ions traveling through the second drift tube to travel multiple times about the closed path.

19. The method of claim 15 wherein one or more of the steps of controlling the set of ion gates comprises controlling the set of ion gates using a processor.

20. The method of claim 15 further comprising an ion detector to detect ions exiting the ion outlet of the first drift tube and produce an ion detection signal corresponding thereto,
   and wherein the method further comprises:
   generating ions prior to introducing the ions into the ion inlet of the first drift tube, and
   processing the ion detection signal to produce ion mobility spectral information as a function of ion drift time.

* * * * *